(12) United States Patent
Hwang et al.

(10) Patent No.: US 10,576,057 B2
(45) Date of Patent: Mar. 3, 2020

(54) METHODS FOR TREATING MUSCLE WASTING AND DEGENERATION DISEASES

(71) Applicant: NEWTREE CO., LTD., Gyeonggi-do (KR)

(72) Inventors: Jae-Kwan Hwang, Seoul (KR); Mi-Bo Kim, Seoul (KR); Changhee Kim, Seoul (KR); Doun Kim, Gyeonggi-do (KR); Heechul Chung, Gyeonggi-do (KR)

(73) Assignee: NEWTREE CO., LTD., Gyeonggi-Do (KR)

( * ) Notice: Subject to any disclaimer, the term of this patent is extended or adjusted under 35 U.S.C. 154(b) by 57 days.

(21) Appl. No.: 15/822,533

(22) Filed: Nov. 27, 2017

(65) Prior Publication Data

US 2018/0153852 A1 Jun. 7, 2018

Related U.S. Application Data

(63) Continuation of application No. PCT/KR2016/005585, filed on May 26, 2016.

(30) Foreign Application Priority Data

May 26, 2015 (KR) .................. 10-2015-0072738

(51) Int. Cl.
| | |
|---|---|
| *A61K 36/605* | (2006.01) |
| *A61K 31/352* | (2006.01) |
| *A21D 2/36* | (2006.01) |
| *A23L 33/105* | (2016.01) |
| *A21D 13/80* | (2017.01) |
| *A61P 21/00* | (2006.01) |
| *A23G 3/48* | (2006.01) |
| *A23G 4/06* | (2006.01) |
| *A23L 2/52* | (2006.01) |

(52) U.S. Cl.
CPC .............. *A61K 31/352* (2013.01); *A21D 2/36* (2013.01); *A21D 2/366* (2013.01); *A21D 13/80* (2017.01); *A23G 3/48* (2013.01); *A23G 4/068* (2013.01); *A23L 2/52* (2013.01); *A23L 33/105* (2016.08); *A61K 36/605* (2013.01); *A61P 21/00* (2018.01); *A23V 2002/00* (2013.01); *A61K 2236/00* (2013.01)

(58) Field of Classification Search
None
See application file for complete search history.

(56) References Cited

U.S. PATENT DOCUMENTS

| | | | |
|---|---|---|---|
| 2008/0096827 A1* | 4/2008 | Jia | A61K 31/353 514/27 |
| 2010/0166898 A1* | 7/2010 | Ku | A61K 31/352 424/775 |
| 2014/0141082 A1 | 5/2014 | Gao | |
| 2018/0099019 A1* | 4/2018 | Brownell | A61K 45/06 |
| 2018/0318320 A1* | 11/2018 | Hwang | A61K 31/575 |
| 2019/0142897 A1* | 5/2019 | Hwang | A61K 9/4833 |

FOREIGN PATENT DOCUMENTS

| KR | 10-2006-0065250 A | 6/2006 |
|---|---|---|
| KR | 10-2010-0114333 A | 10/2010 |

OTHER PUBLICATIONS

De Souza M. et al. Antinociceptive Properties of Morusin, a Prenylfavonoid Isolated from Morus nigra Root Bark. Z Naturforschung 55c:256-260, 2000. (Year: 2000).*
Kim, H. et al. Immunomodulating Activity of a Polysaccharide Isolated rom Mori Cortex Radicis. Archives Pharmacology Research 23(3)240-242, 2000. (Year: 2000).*
International Search Report and Written Opinion in corresponding PCT Application No. PCT/KR2016/005585, dated Nov. 29, 2015.
Ko et al., "Bioactive Constituents of Morus Australis and Broussonetia Papyrifera", Journal of Natural Products, 1997, vol. 60, No. 10, pp. 1008-1011.
McKinnell et al., "Molecular Mechanisms of Muscle Atrophy," Cell, 119, pp. 907-910, (2004).
Lee et al., "The role of hormones, cytokines and heat shock proteins during age-related muscle loss," Clinical Nutrition (2007) 26, pp. 524-534.
Nader, "Molecular determinants of skeletal muscle mass: getting the "AKT" together," The International Journal of Biochemistry & Cell Biology 37 (2005), pp. 1985-1996.
Han et al., "Change of mTOR, p70S6K, 4E-BP1, and AMPK protein expressions with a intensive endurance exercise in rats," The Korea Journal of Sports Science 2011, vol. 20, No. 3, pp. 1551-1561.
Hornberger, "Mechanotransduction and the regulation of mTORC1 signaling in skeletal muscle," The International Journal of Biochemistry & Cell Biology 43 (2011), pp. 1267-1276.
Bonaldo, "Cellular and molecular mechanisms of muscle atrophy," Disease Models & Mechanisms 6, pp. 25-39 (2013) doi:10.1242/dmm.010389.

(Continued)

*Primary Examiner* — Ralph J Gitomer
(74) *Attorney, Agent, or Firm* — Leason Ellis LLP

(57) ABSTRACT

The present invention relates to a composition for preventing and treating muscle diseases or improving muscular function, containing, as an active ingredient, at least one selected from the group consisting of morusin, kuwanon G, and a Mori Cortex Radicis extract. The Mori Cortex Radicis extract, morusin, or kuwanon G, according to the present invention, has an effect of remarkably enhancing muscular function by increasing the expression of p-mTOR protein involved in muscular protein synthesis, inhibiting the expression of mRNAs of MuRF-1 and atrogin-1 involved in muscular protein degradation, and increasing the expression of mRNAs of MyoD and myogenin involved in muscular differentiation. In addition, the present invention is a natural product so as to be used safely without side effects, thereby being usable in drugs, food, or cosmetics.

8 Claims, 5 Drawing Sheets
Specification includes a Sequence Listing.

(56) References Cited

OTHER PUBLICATIONS

Zanou, et al., "Skeletal muscle hypertrophy and regeneration: interplay between the myogenic regulatory factors (MRFs) and insulin-like growth factors (IGFs) pathways," Cellular and Molecular Life Sciences, (2013) 70: pp. 4117-4130.

Yang, et al., "Anti-adipogenic effect of mulberry leaf ethanol extract in 3T3-L1 adipocytes," Nutrition Research and Practice 2014;8(6): pp. 613-617.

Jeong, et al., "Protective Effect of Mulberry and Lithospermum erythrorhizon Extracts on Anti-aging against Photodamage," J Korean Soc Food Sci Nutr, 42(11), pp. 1744-1752 (2013).

Singab, et al., "Hypoglycemic effect of Egyptian Morus alba root bark extract: Effect on diabetes and lipid peroxidation of streptozotocin-induced diabetic rats," Journal of Ethnopharmacology 100 (2005), pp. 333-338.

Chang, et al., "Antioxidant and antityrosinase activity of mulberry (*Morus alba* L.) twigs and root bark," Food and Chemical Toxicology 49 (2011), pp. 785-790.

Kang, et al., "Prediction of tyrosinase inhibitory activities of Morus alba root bark extracts from HPLC fingerprints," Microchemical Journal 110 (2013), pp. 731-738.

Pang, et al., Antibacterial activity of 10 phenolic compounds from mulberry, Journal of China Pharmaceutical University, 2014, 45(2): pp. 221-226.

Yang, et al., "Inhibitory Effects of Constituents from *Morus alba* var. multicaulis on Differentiation of 3T3-L1 Cells and Nitric Oxide Production in RAW264.7 Cells," Molecules 2011, 16, pp. 6010-6022.

Lin, et al., "Antitumor progression potential of morusin suppressing STAT3 and NFkB in human hepatoma SK-Hep1 cells," Toxicology Letters 232 (2015), pp. 490-498.

Park, et al., "Kuwanon G: an antibacterial agent from the root bark of Morus alba against oral pathogens," Journal of Ethnopharmacology 84 (2003), pp. 181-185.

Sohn, et al., "Antimicrobial and cytotoxic activity of 18 prenylated flavonoids isolated from medicinal plants: *Morus alba* L., Morus mongolica Schneider, *Broussnetia papyrifera* (L) Vent, Sophora flavescens Ait and Echinosophora koreensis Nakai," Phytomedicine 11 (2004), pp. 666-672.

\* cited by examiner

METHODS FOR TREATING MUSCLE WASTING AND DEGENERATION DISEASES

TECHNICAL FIELD

The present application claims priority from Korean Patent Application No. 10-2015-0072738, filed on May 26, 2015, the entire contents of which are incorporated herein by reference.

The present invention relates to a composition for preventing and treating muscular diseases or improving muscular function, the composition comprising morusin, kuwanon G, or a Mori Cortex Radicis extract. More specifically, the present invention relates to a composition comprising morusin, kuwanon G, or a Mori Cortex Radicis extract as an active ingredient which has a remarkably effect of preventing and treating muscular diseases or improving muscular function by increasing the expression of p-mTOR protein involved in the synthesis of muscle proteins, inhibiting the mRNA expression of MuRF-1 and atrogin-1 involved in the degradation of muscle proteins, and increasing the mRNA expression of MyoD and myogenin involved in muscular differentiation.

BACKGROUND OF THE INVENTION

Muscle atrophy is caused by a gradual decrease in muscle mass and refers to muscle weakness and degeneration (Cell, 119 (7): 907-910, 2004). Muscle atrophy is accelerated by inactivity, oxidative stress, and chronic inflammation, while weakening muscular function and athletic performance (Clinical Nutrition, 26 (5): 524-534, 2007). The most important factor determining muscular function is muscle mass, which is maintained by a balance of protein synthesis and degradation. Muscular atrophy is caused when protein degradation occurs greater than protein synthesis (The International Journal of Biochemistry and Cell Biology, 37 (10): 1985-1996, 2005).

While the size of a muscle is regulated by intracellular signaling pathways leading to anabolism or catabolism within the muscle, the synthesis of muscle protein increases when the signaling reactions inducing the synthesis of muscle protein are greater than those inducing the degradation of the muscle protein. This occurs as an increase in the number of muscle fibers (hyperplasia) or an increase in the size of muscle (hypertrophy) due to the increase in muscle protein (The Journal of Sports Science, 20 (3): 1551-1561, 2011). Factors involved in muscle protein synthesis induce protein synthesis by phosphorylating downstream proteins based on the stimulation of phosphatidylinositol-3 kinase (PI3K)/Akt pathway in muscle cells. The activation of the mammalian target of rapamycin (mTOR) by PI3K/Akt signaling is recognized as a central growth signaling factor that integrates various growth signals in the cell. mTOR induces muscle protein synthesis by activating two factors that initiate mRNA translation, i.e. 4E-binding protein (4EBP1) and phosphorylated 70-kDa ribosomal S6 kinase (p70S6K), contributing to increase in muscle mass (The Korea Journal of Sports Science, 20 (3): 1551-1561, 2011; The International Journal of Biochemistry and Cell Biology, 43 (9): 1267-1276, 2011). Conversely, when the transcription factor forhead box (FoxO) migrates from the cytoplasm to the nucleus, it increases the expression of the E3 ubiquitin ligase, atrogin-1 and MuRF-1 which are involved in proteolysis (Disease Models and Mechanisms, 6:25-39, 2013). Increasing the expression level of these proteins promotes protein degradation in muscles, resulting in reduced muscle mass. Thus, the activation of mTOR activity and inhibition of atrogin-1 and MuRF-1 expression increase muscle mass by increasing the amount of muscle protein.

Muscle cell differentiation and muscle formation are regulated by a variety of muscle regulatory factors. Among them, MyoD initiates the expression of muscle specific genes and induces the differentiation of muscle satellite cells into myoblasts. Induction of myogenin expression by activation of MyoD is the most important factor in the fusion of myoblasts and is involved in the formation of myotubes. The muscle fibers formed through this process are bundled to finally form muscles (Cellular and Molecular Life Sciences, 70: 4117-4130, 2013).

Mori Cortex Radicis is the dried root bark of *Morus alba* or other plants belonging to a plant of family Moraceae and genus *Morus* spp. The *Morus alba*, which is also called as mulberry, has been reported to possess various effects such as anti-obesity (Nutrition Research and Practice, 8 (6): 613-617, 2014), anti-photoaging (Journal of Korea Society of Food Science and Nutrition, 42(11): 1744-1752, 2013), anti-diabetes (Journal of Ethnopharmacology, 100 (3): 333-338, 2005), and anti-oxidant and skin whitening effects (Food and Chemical Toxicology, 49 (4): 785-790, 2011).

Morusin and kuwanon G are flavones found primarily in Mori Cortex Radicis, respectively (Microchemical Journal, 110: 731-738, 2013). Morusin has been reported to possess such effects as anti-microbial effect (Journal of China Pharmaceutical University, 45(2): 221-226, 2014), anti-obesity effect (Molecule, 16(7): 6010-6022, 2011), and anti-cancer effect (Toxicology Letters 232(2): 490-498, 2015). In addition, it has been reported that kuwanon G possesses an anti-bacterial effect (Journal of Ethnopharmacology, 84 (2-3): 181-5, 2003; Phytomedicine, 11 (7-8): 666-672, 2004).

However, prior to the present invention, there has been no report on the prevention or treatment of muscular diseases or the improvement of muscular function of Mori Cortex Radicis, morusin, or kuwanon G.

DETAILED DESCRIPTION OF THE INVENTION

Technical Problem

While having searched for natural substances which are excellent in controlling muscle functions and can safely be applied, the present inventors have completed the present invention by confirming that morusin, kuwanon G, or an extract of Mori Cortex Radicis has an activity of preventing or treating muscle diseases or improving muscular function.

Accordingly, an aspect of the present invention is to provide a pharmaceutical composition for preventing or treating muscle diseases, the composition comprising, as an active ingredient, at least one selected from the group consisting of a compound of Formula 1 and a compound of Formula 2, and an extract of Mori Cortex Radicis:

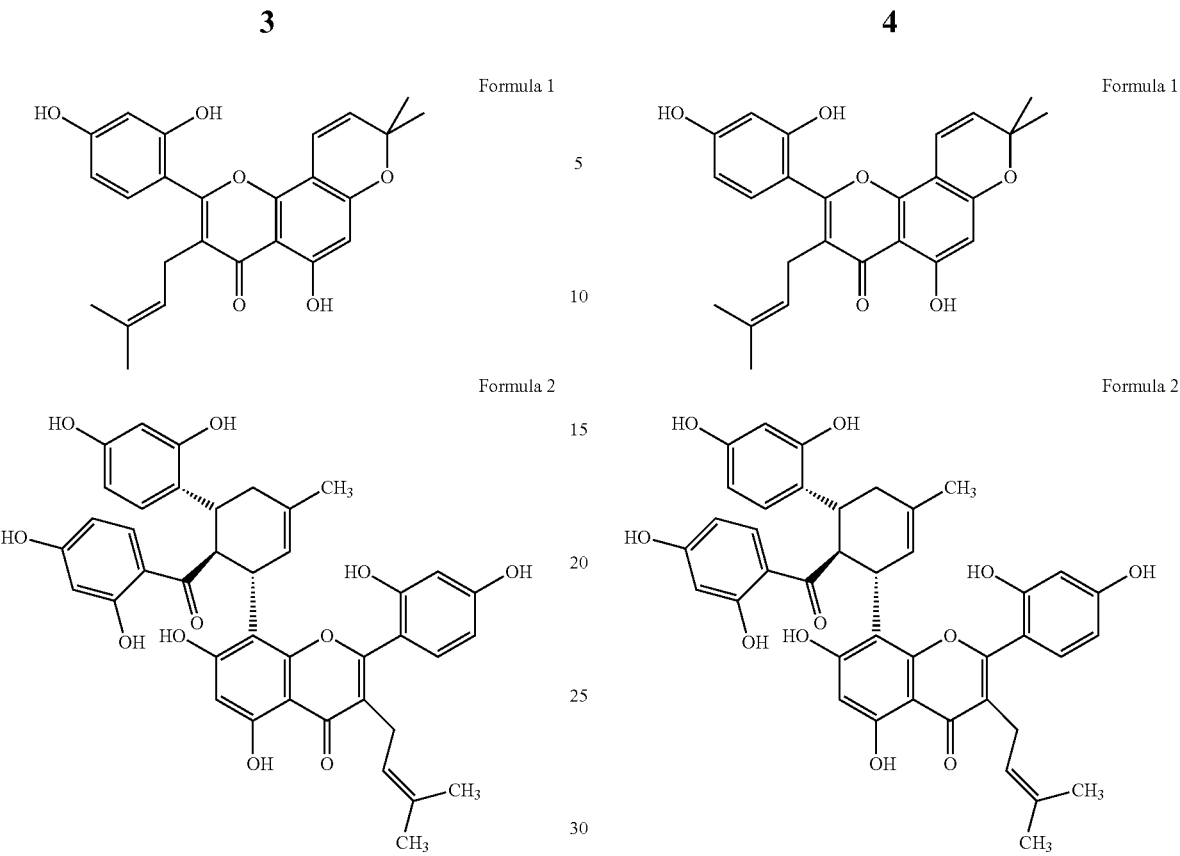

Another aspect of the present invention is to provide a food composition for preventing muscle diseases or improving muscular function, the composition comprising, as an active ingredient, at least one selected from the group consisting of a compound of the Formula 1 and a compound of the Formula 2, and an extract of Mori Cortex Radicis.

Another aspect of the present invention is to provide a cosmetic composition for improving muscle function, the composition comprising, as an active ingredient, at least one selected from the group consisting of a compound of the Formula 1 and a compound of the Formula 2, and an extract of Mori Cortex Radicis.

Still another aspect of the present invention is to provide a use of at least one selected from the group consisting of a compound of the Formula 1 and a compound of the Formula 2, and an extract of Mori Cortex Radicis for the preparation of an agent for preventing or treating muscular diseases.

Still further another aspect of invention is to provide a method for preventing or treating muscle diseases, the method comprising administering an effective amount of at least one selected from the group consisting of a compound of the Formula 1 and a compound of the Formula 2, and an extract of Mori Cortex Radicis to a subject in need thereof.

Technical Solution

An embodiment according to an aspect of the present invention provides a pharmaceutical composition for preventing or treating muscle diseases, the composition comprising, as an active ingredient, at least one selected from the group consisting of a compound of Formula 1 and a compound of Formula 2, and an extract of Mori Cortex Radicis:

Another embodiment according to an aspect of the present invention provides a food composition for preventing muscle diseases or improving muscular function, the composition comprising, as an active ingredient, at least one selected from the group consisting of a compound of the Formula 1 and a compound of the Formula 2, and an extract of Mori Cortex Radicis.

Still another embodiment according to an aspect of the present invention provides a cosmetic composition for improving muscle function, the composition comprising, as an active ingredient, at least one selected from the group consisting of a compound of the Formula 1 and a compound of the Formula 2, and an extract of Mori Cortex Radicis.

Still another embodiment according to an aspect of the present invention provides a use of at least one selected from the group consisting of a compound of the Formula 1 and a compound of the Formula 2, and an extract of Mori Cortex Radicis for the preparation of an agent for preventing or treating muscular diseases.

Still further another embodiment according to an aspect of the present invention provides a method for preventing or treating muscle diseases, the method comprising administering an effective amount of at least one selected from the group consisting of a compound of the Formula 1 and a compound of the Formula 2, and an extract of Mori Cortex Radicis to a subject in need thereof.

Hereinafter, the present invention will be described in detail.

An embodiment according to an aspect of the present invention provides a pharmaceutical composition for preventing or treating muscle diseases, the composition comprising, as an active ingredient, at least one selected from the group consisting of a compound of Formula 1 and a compound of Formula 2, and an extract of Mori Cortex Radicis:

Formula 1

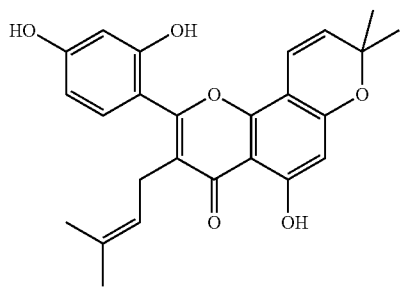

Formula 2

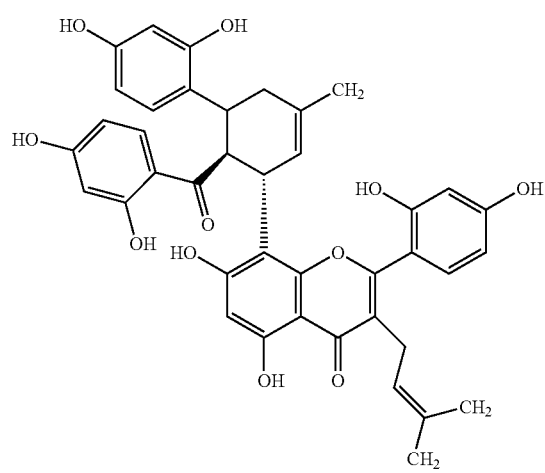

As used herein, the above-mentioned Mori Cortex Radicis is the dried root bark of *Morus alba* or other plants belonging to a plant of family Moraceae and genus *Morus* spp.

In one example of the present invention, morusin, a compound represented by Formula 1 and kuwanon G, a compound represented by Formula 2, were isolated from Mori Cortex Radicis. Morusin, kuwanon G, and an extract of Mori Cortex Radicis, respectively, have a remarkable effect of increasing muscle mass by increasing the expression of p-mTOR protein involved in the synthesis of muscle proteins, inhibiting the mRNA expression of MuRF-1 and atrogin-1 involved in the degradation of muscle proteins, and increasing the mRNA expression of MyoD and myogenin involved in muscular differentiation.

A compound of Formula 1 or a compound of Formula 2 may be isolated from a plant extract or chemically synthesized, or may be a commercially available compound.

As used herein, a compound represented by Formula 1 or a compound represented by Formula 2 may be isolated from an extract of Mori Cortex Radicis extract. The compound represented by Formula 1 or the compound represented by Formula 2 may be isolated from Mori Cortex Radicis.

The extract of Mori Cortex Radicis according to the present invention can be extracted by known natural material extraction methods. Preferably, it may be extracted by using one or more solvents selected from the group consisting of water, organic solvents having 1 to 6 carbon atoms, and subcritical or supercritical fluids. The organic solvent having 1 to 6 carbon atoms may be selected from the group consisting of alcohol having 1 to 6 carbon atoms, acetone, ether, benzene, chloroform, ethyl acetate, methylene chloride, hexane, cyclohexane, and petroleum ether, but is not limited thereto.

In addition, the extract of Mori Cortex Radicis according to the present invention can be obtained by extracting and purifying dried Mori Cortex Radicis using purified water, ethanol, supercritical carbon dioxide, or supercritical carbon dioxide suitable for food processing, or using ultra-high pressure extraction devices. Alternatively, it can be obtained by separating and purifying an oil obtained by direct compression of Mori Cortex Radicis. For example, the extract can be obtained by compressing Mori Cortex Radicis under an ultra-high pressure condition of 100 Mpa or more. Preferably, the pressure may be in the range of 100 MPa to 1,000 Mpa which is an ultra-high pressure condition, but is not limited thereto.

As used herein, the term 'muscle' refers collectively to the sinews, muscles, and tendons, while the term 'muscular function' refers to the ability of the muscle to exert its force by contraction of muscle. The muscular function includes muscular strength which is the ability of the muscle to exert its maximum contractility to overcome resistance, muscular endurance which is the ability of the muscle indicating how long or how many times the muscle can repeat contraction and relaxation on a given weight, and explosive muscular strength which is the ability of the muscle to exert a strong force in a short period of time. These muscular functions are managed by the liver and are proportional to muscle mass. The term 'the improvement of muscular function' refers to enhancement or betterment of muscular function.

The pharmaceutical composition for preventing and treating muscle diseases of the present invention can be used for preventing or treating muscle diseases due to muscle wasting or degeneration. Muscle wasting and degeneration are caused by genetic factors, acquired factors, aging or the like. Muscle wasting is characterized by gradual loss of muscle mass, weakness and degeneration of muscles, especially skeletal muscles or voluntary muscles and heart muscles. Examples of such diseases include atony, muscular atrophy, muscular dystrophy, muscular degeneration, muscular spasticity, amyotrophic lateral sclerosis, myasthenia gravis, cachexia, sarcopenia and the like, while not being limited thereto. The composition of the present invention has an effect of increasing muscle mass, while the type of muscles is not limited.

The composition for preventing or treating muscular diseases or improving muscular function of the present invention may contain the extract of Mori Cortex Radicis alone or further contain at least one active ingredient which exhibits a similar function to the extract of Mori Cortex Radicis. The inclusion of additional active ingredients may further enhance the effect of improving muscular function in accordance with the composition of the present invention. In case where additional active ingredients are added as described above, skin safety, easiness of formulation, and stability of active ingredients due to such a combined use may be taken into consideration.

For the purpose of a bodily administration, the composition according to the present invention may be prepared in the form of a pharmaceutical composition such as an oral administration agent, a transdermal administration agent, and an inhaled administration agent, in the form of a food composition such as a functional food, a nutritional supplement, a health food and a food additive, or in the form of a cosmetic composition.

The compound of Formula 1, the compound of Formula 2 or the extract of Mori Cortex Radicis according to the present invention is excellent in preventing and treating muscle diseases or improving muscular function.

The composition of the present invention is effective in promoting the increase of muscle mass, while the types of muscle are not limited. Increasing muscle mass is to improve the performance of body constituents, especially muscle. Muscle mass can be increased through physical exercise and the improvement of endurance and by administering a substance with its effect of muscle growth to the body.

The compound of Formula 1, the compound of Formula 2 or the extract of Mori Cortex Radicis according to the present invention is excellent in increasing muscle mass, respectively, and thus can be used as an active ingredient of a pharmaceutical composition.

Further, the compound of Formula 1, the compound of Formula 2 or the extract of Mori Cortex Radicis according to the present invention is excellent in increasing muscle mass, respectively, and thus can be used as an active ingredient of a food composition.

In addition, the compound of Formula 1, the compound of Formula 2 or the extract of Mori Cortex Radicis according to the present invention is excellent in increasing muscle mass, respectively, and thus can be used as an active ingredient of a cosmetic composition.

The pharmaceutical composition of the present invention may contain a pharmaceutically acceptable salt of the compound of Formula 1, the compound of Formula 2 or the extract of Mori Cortex Radicis. As used herein, the term 'pharmaceutically acceptable' refers to one which is physiologically acceptable and does not normally cause an allergic reaction or similar reaction when administered to humans, wherein the salt is preferably an acid addition salt formed by a pharmaceutically acceptable free acid.

The pharmaceutically acceptable salt of the compound of Formula 1, the compound of Formula 2 or the extract of Mori Cortex Radicis may be an acid addition salt formed using an organic acid or an inorganic acid. The organic acid may be, for example, formic acid, acetic acid, propionic acid, lactic acid, butyric acid, isobutyric acid, trifluoroacetic acid, malic acid, maleic acid, malonic acid, fumaric acid, succinic acid, succinic monoamide, glutamic acid, tartaric acid, oxalic acid, citric acid, glycolic acid, glucuronic acid, ascorbic acid, benzoic acid, phthalic acid, salicylic acid, anthranilic acid, dichloroacetic acid, aminooxyacetic acid, benzenesulfonic acid, p-toluenesulfonic acid or methanesulfonic acid. The inorganic acid comprises, for example, hydrochloric acid, bromic acid, sulfuric acid, phosphoric acid, nitric acid, carbonic acid or boric acid. The acid-addition salt may preferably be in the form of a hydrochloride or acetate, more preferably in the form of a hydrochloride.

The above mentioned acid-addition salts may be prepared by conventional salt preparation methods such as a) directly mixing the compound of Formula 1, the compound of Formula 2 or the extract of Mori Cortex Radicis with an acid, b) dissolving one of them in a solvent or a water-containing solvent, followed by mixing, and c) placing the compound of Formula 1, the compound of Formula 2 or the extract of Mori Cortex Radicis in a solvent or an acid in a hydrated solvent, followed by mixing.

Apart from the above, additional salt forms include the salts of gamma-aminobutyric acid (GABA), gabapentin, pregabalin, nicotinate, adipate, hemimarate, cysteine, acetylcysteine, methionine, arginine, lysine, ornithine or aspartate.

In addition, the pharmaceutical composition for preventing and treating muscle diseases of the present invention may further comprise a pharmaceutically acceptable carrier.

The pharmaceutically acceptable carrier may further include, for example, a carrier for oral or parenteral administration. Carriers for oral administration may include lactose, starch, cellulose derivatives, magnesium stearate, stearic acid, and the like. Carriers for parenteral administration may include water, suitable oils, saline, aqueous glucose and glycols and the like. In addition, stabilizers and preservatives may be further included. Suitable stabilizers may be antioxidants such as sodium hydrogen sulfite, sodium sulfite and ascorbic acid. Suitable preservatives may include benzalkonium chloride, methyl- or propyl-paraben and chlorobutanol. Other pharmaceutically acceptable carriers may be referred to those described in the following reference (Remington's Pharmaceutical Sciences, 19th ed., Mack Publishing Company, Easton, Pa., 1995).

The pharmaceutical composition of the present invention can be administered to mammals including humans by any method. For example, it can be administered orally or parenterally, while parenteral administration methods may include, but are not limited to, intravenous, intramuscular, intra-arterial, intramedullary, intrathecal, intracardiac, transdermal, subcutaneous, peritoneal, intranasal, enteral, topical, sublingual or rectal administration.

The pharmaceutical composition of the present invention may be formulated into oral or parenteral dosage forms according to the route of administration as described above. When formulated, it is prepared by one or more buffers (e. g., saline or PBS), antioxidants, bacteriostats, chelating agents (e. g., EDTA or glutathione), fillers, extenders, binders, adjuvants (e.g., aluminum hydroxide), suspending agents, thickening agents, wetting agents, disintegrating agents or surfactants, diluents or excipients.

Solid formulations for oral administration include tablets, pills, powders, granules, solutions, gels, syrups, slurries, suspensions or capsules. These solid formulations can be prepared by mixing the pharmaceutical composition of the present invention with at least one excipient, for example, starch (including corn starch, wheat starch, rice starch and potato starch), calcium carbonate, sucrose, lactose, dextrose, sorbitol, mannitol, xylitol, erythritol maltitol, cellulose, methyl cellulose, sodium carboxymethyl cellulose and hydroxypropylmethyl-cellulose or gelatin. For instance, tablets or sugar-coated tablets can be obtained by combining the active ingredient with a solid excipient, then milling it, adding suitable auxiliaries, and processing the mixture into granules.

In addition to simple excipients, lubricants such as magnesium stearate talc are also used. Liquid preparations for oral administration include suspensions, solutions, emulsions or syrups. In addition to commonly used simple diluents such as water or liquid paraffin, various excipients such as wetting agents, sweetening agents, fragrances or preservatives may be included.

In addition, crosslinked polyvinylpyrrolidone, agar, alginic acid or sodium alginate may be added as a disintegrant depending on formulations, and may further include an anti-coagulant, a lubricant, a wetting agent, a fragrance, an emulsifier and an antiseptic agent.

When administered parenterally, the pharmaceutical composition of the present invention can be formulated in accordance with methods known in the art in the form of injections, transdermal agents, and nasal inhalers, together with suitable parenteral carriers. In the case of the injections, they must be sterilized and protected from contamination of microorganisms such as bacteria and fungus. Examples of suitable carriers for injectable formulations include, but are not limited to, solvents or dispersion media containing water, ethanol, polyols (such as glycerol, propylene glycol and liquid polyethylene glycol, etc.), mixtures thereof and/or vegetable oils. More preferably, suitable carriers include, but are not limited to, Hank's solution, Ringer's solution, phosphate buffered saline (PBS) containing triethanolamine or sterile water for injection, 10% ethanol, 40% propylene glycol and 5% dextrose. To protect the injection from microbial contamination, various antibacterial and antifungal agents such as parabens, chlorobutanol, phenol, sorbic acid, and thimerosal may be further included. Alternatively, the injectable formulation may mostly further contain an isotonic agent, such as sugar or sodium chloride.

Examples of transdermal dosage forms include ointments, creams, lotions, gels, solutions for external use, pastes, liniments, and aerosols. As used herein, the term 'transdermal administration' means that a pharmaceutical composition is topically administered to the skin, whereby an effective amount of the active ingredient contained in the pharmaceutical composition is delivered into the skin.

In the case of an inhalation dosage form, the compound used in accordance with the present invention may be conveniently delivered in the form of an aerosol spray from a pressurized pack or nebulizer, while using a suitable propellant, such as dichlorofluoromethane, trichlorofluoromethane, dichlorotetrafluoroethane, carbon dioxide and other suitable gas. In the case of a pressurized aerosol, the dosage unit may be determined by providing a valve that delivers a metered amount. For example, gelatin capsules and cartridges used for an inhaler or insufflator may be formulated to contain a compound, and a powder mixture of a suitable powder base such as lactose or starch. Formulations for parenteral administration are described in the literature (Remington's Pharmaceutical Science, 15th Edition, 1975. Mack Publishing Company, Easton, Pa. 18042, Chapter 87: Blaug, Seymour) as a generally known form of pharmaceutical chemistry.

The pharmaceutical composition according to the present invention for the prevention and treatment of muscle diseases can provide a desirable preventative and therapeutic effects for muscle diseases when the compound of Formula 1, the compound of Formula 2 or the extract of Mori Cortex Radicis is contained in its effective amount. As used herein, 'the effective amount' refers to an amount that exhibits an effect greater than that of the negative control, and preferably refers to an amount sufficient to improve muscular function. The pharmaceutical composition of the present invention may contain 0.01 to 99.99% of the compound of Formula 1, the compound of Formula 2 or the extract of Mori Cortex Radicis, while the remaining amount may be a pharmaceutically acceptable carrier. The effective amount of the compound of Formula 1, the compound of Formula 2 or the extract of Mori Cortex Radicis contained in the pharmaceutical composition of the present invention will vary depending on a form into which the composition is formulated or the like.

The total effective amount of the pharmaceutical composition of the present invention may be administered to a patient in a single dose and may be administered by a fractionated treatment protocol administered over a prolonged period of time in multiple doses. The pharmaceutical composition of the present invention may vary in the content of the active ingredient depending on the severity of the disease. When administered parenterally, it is preferably administered in an amount of 0.01 to 50 mg, more preferably 0.1 to 30 mg per 1 kg of body weight per day on the basis of the compound of Formula 1, the compound of Formula 2 or the extract of Mori Cortex Radicis. When administered orally, it may be administered in one to several divided doses so as to be preferably administered in an amount of 0.01 to 100 mg, more preferably 0.01 to 10 mg per kg of body weight per day on the basis of the compound of Formula 1, the compound of Formula 2 or the extract of Mori Cortex Radicis. However, the dose of the compound of Formula 1, the compound of Formula 2 or the extract of Mori Cortex Radicis is determined depending on various factors including the route of administration and the number of treatments of the pharmaceutical composition as well as the patient's age, body weight, health condition, sex, severity of disease, diet and excretion rate. Accordingly, those of ordinary skill in the art will be able to determine the appropriate effective dose for the particular use for the prevention and treatment of muscle diseases. The pharmaceutical composition according to the present invention is not particularly limited to formulations, administration routes and administration methods as long as the effect of the present invention is exhibited.

The pharmaceutical composition according to the present invention for the prevention and treatment of muscle diseases can be used alone or in combination with methods using surgery, radiation therapy, hormone therapy, chemical therapy or a biological response modifier.

The pharmaceutical composition according to the present invention for the prevention and treatment of muscle diseases can also be provided as a formulation of an external agent containing the compound of Formula 1, the compound of Formula 2 or the extract of Mori Cortex Radicis as an active ingredient.

When the pharmaceutical composition of the present invention for the prevention and treatment of muscle diseases is used as an external preparation for skin, it may further contain adjuvants commonly used in the field of dermatology, for instance any ingredients conventionally used in dermatological external preparations such as fatty substances, organic solvents, solubilizers, thickening agents, gelling agents softeners, antioxidants, suspending agents, stabilizers, foaming agents, fragrant agents, surfactants, water, ionic emulsifiers, non-ionic emulsifiers, fillers, sequestering agents, chelating agents, preservatives, vitamins, blocking agents, wetting agents, essential oils, dyes, pigments, hydrophilic active agents, lipophilic active agents, lipids vesicles and the like. Such components may be contained in amounts commonly used in the field of dermatology.

When the pharmaceutical composition according to the present invention for preventing and treating muscle diseases is provided as an external preparation for skin, it may be a formulation such as ointments, patches, gels, creams or sprays.

The present invention also provides a food composition for preventing muscle diseases or improving muscular function, the composition comprising, as an active ingredient, at least one selected from the group consisting of a compound of Formula 1, a compound of Formula 2 or an extract of Mori Cortex Radicis:

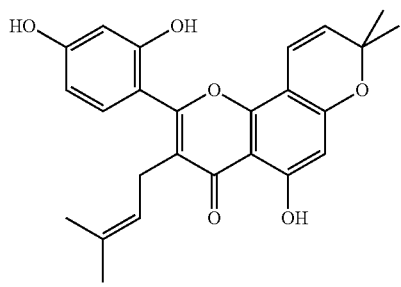

Formula 1

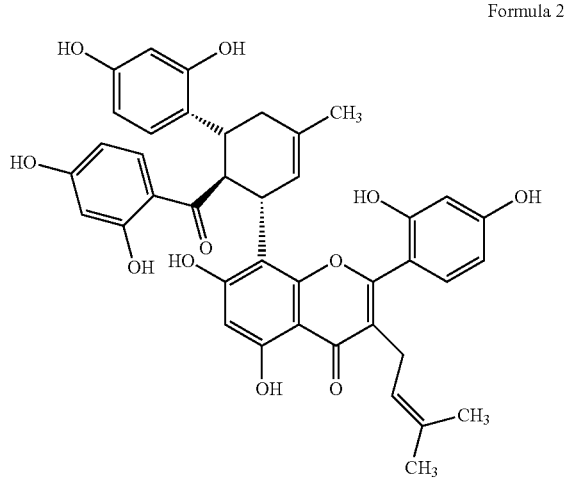

Formula 2

The food composition of the present invention includes all forms of functional foods, nutritional supplements, health foods, food additives and feeds for consumption by humans or animals including livestock. Such types of Food compositions may be prepared in a variety of forms according to conventional methods known in the art.

The food compositions can be prepared in a variety of forms according to conventional methods known in the art. The *Platycodon grandiflorum* extract may be added into common foods which include, but are not limited to, beverages (e.g., alcoholic beverages), fruits and processed foods thereof (e.g., canned fruits, bottled jam, and marmalade), fish, meat and processed foods thereof (e.g., ham and corn beef sausage), breads and noodles (e.g., udon, buckwheat noodles, ramen noodles, spaghetti, and macaroni), juice, various drinks, cookies, taffy, dairy product (e.g., butter and cheese), edible vegetable oil, margarine, vegetable protein, retort food, frozen food, and various kinds of seasoning (e.g., soybean paste, soy sauce, and sauce). The compound of Formula 1, the compound of Formula 2 or the extract of Mori Cortex Radicis may be added into nutritional supplements which include, but are not limited to, capsules, tablets, and pills. In addition, the health functional food may be prepared, but are not limited to, by liquifying, granulating, encapsulating or pulverizing the extract of Mori Cortex Radicis so that the extract of Mori Cortex Radicis per se can be prepared in the form of teas, juices, and drinks for consumption. In addition, in order to use the extract of Mori Cortex Radicis as a food additive, it may be used in the form of powder or concentrated liquid. Furthermore, it can be prepared in the form of a composition by mixing together the extract of Mori Cortex Radicis and a known active ingredient effective in the prevention of muscle diseases and improvement of muscular function.

When the composition of the present invention for preventing muscle diseases and improving muscular function is used as a health beverage composition, the health beverage composition may contain various flavors or natural carbohydrates as additional ingredients as in conventional beverages. The above-mentioned natural carbohydrates include monosaccharides such as glucose and fructose; disaccharides such as maltose and sucrose: polysaccharides such as dextrins and cyclodextrins: sugar alcohols such as Xylitol, sorbitol, and erythritol. Sweeteners include natural sweeteners such as the extracts of thaumatin and stevia: synthetic sweeteners such as saccharin and aspartame. The ratio of the natural carbohydrate is generally about 0.01 g to 0.04 g, preferably about 0.02 g to 0.03 g per 100 mL of the composition of the present invention.

The compound of Formula 1, the compound of Formula 2 or the extract of Mori Cortex Radicis may be contained as an active ingredient of a food composition for the prevention of muscle diseases and improvement of muscular function. The effective amount thereof is preferably, but is not particularly limited to, 0.01% to 100% of the total weight of the composition. The food composition of the present invention may be prepared by mixing the compound of Formula 1, the compound of Formula 2 or the extract of Mori Cortex Radicis with other active ingredient known to be effective in preventing muscle diseases and improving muscular function.

In addition, the health food of the present invention may contain various nutrients, vitamins, electrolytes, flavors, colorants, pectic acid, salts of pectic acid, alginic acid, salts of alginic acid, organic acid, protective colloid thickener, pH adjuster, stabilizer, glycerin, an alcohol or a carbonating agent. In addition, the health food of the present invention may contain pulps for the production of natural fruit juice, fruit juice drink or vegetable drink. These components may be used independently or in combination. The proportion of such additives is not critical, but is generally selected in the range of 0.01 to 0.1 parts by weight per 100 parts by weight of the composition of the present invention.

The present invention also provides a cosmetic composition for improving muscular function, the composition comprising at least one selected from the group consisting of a compound of Formula 1, a compound of Formula 2 or an extract of Mori Cortex Radicis:

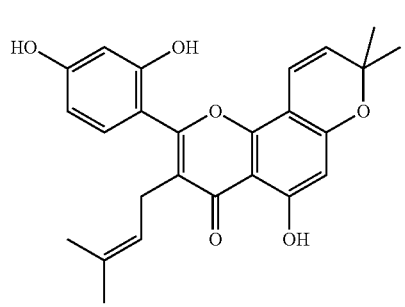

Formula 1

Formula 2

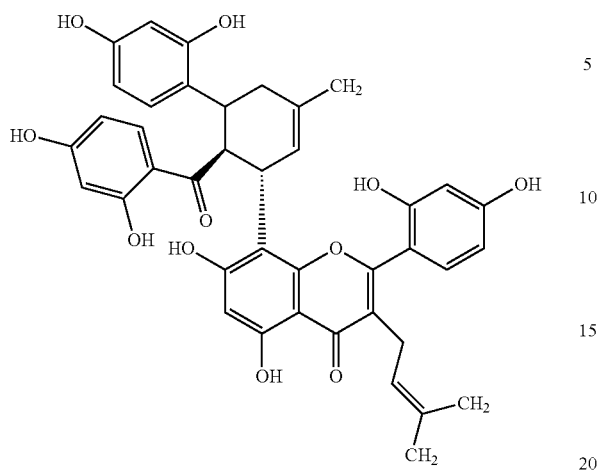

The cosmetic composition of the present invention contains at least one selected from the group consisting of the compound of Formula 1, the compound of Formula 2 or the extract of Mori Cortex Radicis as an active ingredient and may be prepared into basic cosmetic composition (e.g., lotion, cream, essence, cleanser such as cleansing foam and cleansing water, pack, and body oil), color cosmetic composition (e.g., foundation, lipstick, mascara, and make-up base), hair product composition (e.g., shampoo, rinse, hair conditioner, and hair gel), soap or the like together with dermatologically acceptable excipients.

Such excipients include, but are not limited to, for example, emollients, skin penetration enhancers, colorants, fragrants, emulsifiers, thickeners, and solvents. In addition, it may further contain perfumes, coloring matters, bactericides, antioxidants, preservatives, and moisturizers, and may include thickeners, inorganic salts, and synthetic polymeric substances for the purpose of improving physical properties. For example, when cleansers and soap are prepared with the cosmetic composition of the present invention, they may be easily prepared by adding the extract of Mori Cortex Radicis to a common cleanser and a soap base. In the case of producing a cream, it can be prepared by adding the extract of Mori Cortex Radicis or its salt to a cream base of a typical underwater type (O/W). A synthetic or natural material such as a protein, a mineral, or a vitamin may be further added for the purpose of improving physical properties with a flavor, a chelating agent, a pigment, an antioxidant, and an antiseptic.

The content of the compound of Formula 1, the compound of Formula 2 or the extract of Mori Cortex Radicis contained in the cosmetic composition of the present invention is not limited thereto, but is preferably 0.001 to 10% by weight, more preferably 0.01 to 5% by weight based on the total weight of the whole composition. If the content is less than 0.001% by weight, the desired effect of improving muscular function may not be expected. If the content is more than 10% by weight, it may be difficult to manufacture in terms of safety or preparation of formulation.

The present invention provides a use of at least one selected from the group consisting of a compound of Formula 1, a compound of Formula 2 or an extract of Mori Cortex Radicis for the preparation of an agent for preventing or treating muscle diseases:

Formula 1

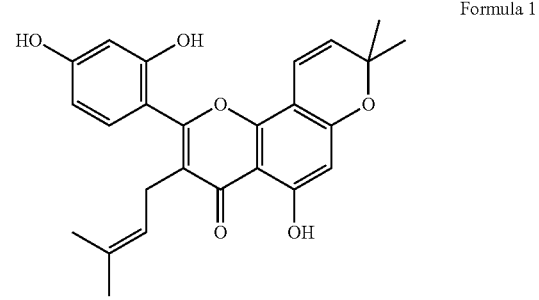

Formula 2

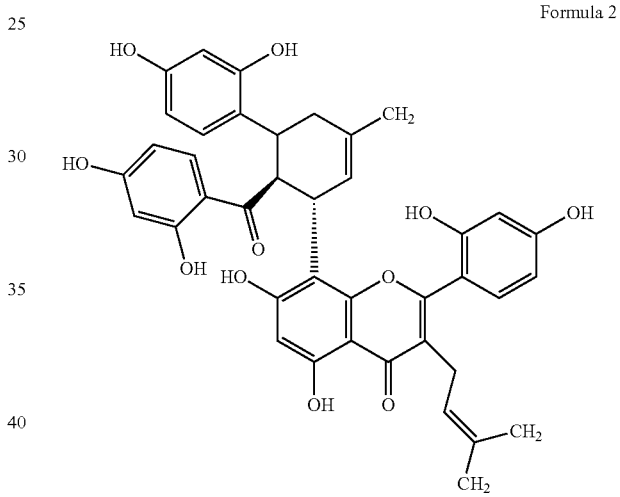

The present invention provides a method for preventing or treating muscle diseases, the method comprising administering an effective amount of at least one selected from the group consisting of a compound of Formula 1, a compound of Formula 2 or an extract of Mori Cortex Radicis to a subject in need thereof:

Formula 1

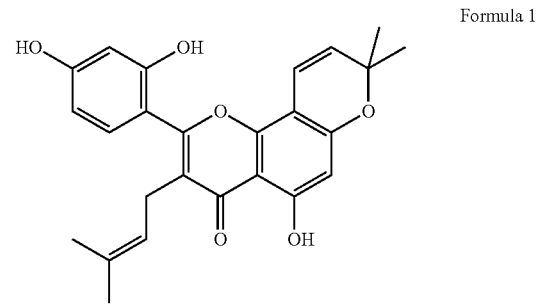

-continued

Formula 2

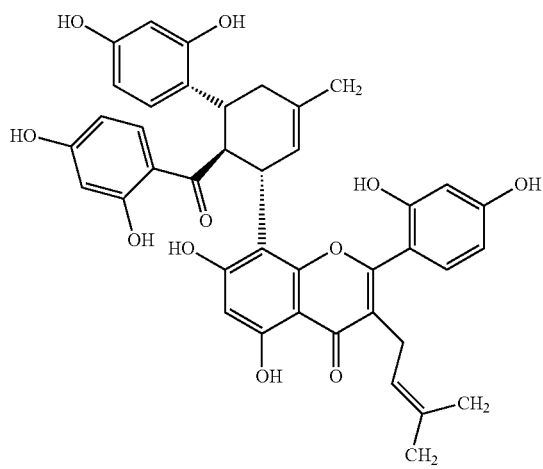

As used herein, the term "effective amount" refers to an amount that, when administered to a subject, leads to the improvement, treatment, or prevention of muscle diseases. The term "subject" may be an animal, preferably a mammal including humans and livestock, animal-derived cells, tissues, or organs. The subject may be a patient or livestock needed for treatment.

Effects of the Invention

As used herein, morusin, kuwanon G, or the extract of Mori Cortex Radicis has a remarkable effect of increasing muscle mass by increasing the expression of p-mTOR protein involved in the synthesis of muscle proteins, inhibiting the mRNA expression of MuRF-1 and atrogin-1 involved in the degradation of muscle proteins, and increasing the mRNA expression of MyoD and myogenin involved in muscular differentiation. In addition, the present invention is directed to natural substances which can be safely used without any side effects in the forms of medicines, foods, or cosmetics.

MODE FOR CARRYING OUT INVENTION

Figure 1:
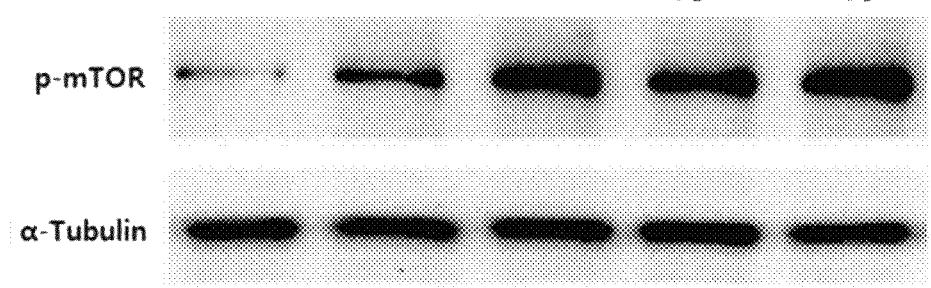
FIG. 1 shows the results of measuring the expression of p-mTOR protein in L6 muscle cells after treating with morusin, kuwanon G, or the extract of Mori Cortex Radicis.

Hereinafter, the present invention will be described in more detail with reference to Examples.

However, the following Examples are illustrative of the present invention, and the scope of the present invention is not limited to the following Examples.

Reference Example 1: Material Information of Morusin

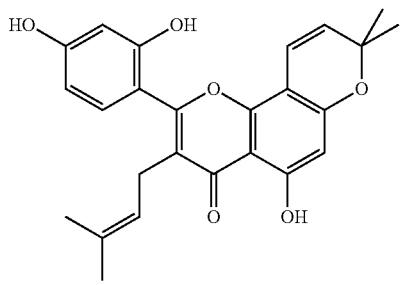 [SMILES: CC(C)=CCc1c(-c2ccc(O)cc2O)oc2c3c(cc(O)c2c1=O)OC(C)(C)C=C3]

Chemical Name: Morusin; 2-(2,4-Dihydroxyphenyl)-5-hydroxy-8,8-dimethyl-3-(3-methyl-2-buten-1-yl)-4H,8H-benzo[1,2-b:3,4-b']dipyran-4-one CAS No.: 62596-29-6

Reference Example 2: Material Information of Kuwanon G

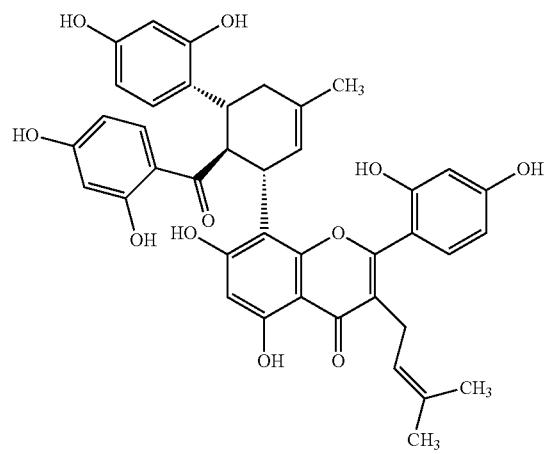

Chemical Name: kuwanon G; 8-[(1S,5R,6S)-6-(2,4-Dihydroxybenzoyl)-5-(2,4-dihydroxyphenyl)-3-methyl-2-cyclohexen-1-yl]-2-(2,4-dihydroxyphenyl)-5,7-dihydroxy-3-(3-methyl-2-buten-1-yl)-4H-chromen-4-one CAS No.: 75629-19-5

Example 1

Preparation of the Extract of Mori Cortex Radicis

<1-1> Preparation of Methanol Extract of Mori Cortex Radicis

The dried Mori Cortex Radicis was pulverized with a mixer, and 100 g of the pulverized Mori Cortex Radicis sample was added to 1 L of 100% methanol and extracted three times at room temperature for 24 hours. The extracted sample was filtered with Whatman No. 2 filter paper under reduced pressure, and the filtered extract was concentrated using a vacuum rotary condenser to remove the solvent component, and then a methanol extract of Mori Cortex Radicis was obtained.

<1-2> Preparation of Ethanol Extract of Mori Cortex Radicis

The dried Mori Cortex Radicis was pulverized with a mixer, and 100 g of the pulverized Mori Cortex Radicis sample was added to 1 L of 100% ethanol and extracted three times at room temperature for 24 hours. The extracted sample was filtered with Whatman No. 2 filter paper under reduced pressure, and the filtered extract was concentrated using a vacuum rotary condenser to remove the solvent component, and then an ethanol extract of Mori Cortex Radicis was obtained.

<1-3> Preparation of Ethyl Acetate Extract of Mori Cortex Radicis

The dried Mori Cortex Radicis was pulverized with a mixer, and 100 g of the pulverized Mori Cortex Radicis sample was added to 1 L of 100% ethyl acetate and extracted three times at room temperature for 24 hours. The extracted sample was filtered with Whatman No. 2 filter paper under reduced pressure, and the filtered extract was concentrated using a vacuum rotary condenser to remove the solvent component, and then an ethyl acetate extract of Mori Cortex Radicis was obtained.

<1-4> Preparation of Hexane Extract of Mori Cortex Radicis

The dried Mori Cortex Radicis was pulverized with a mixer, and 100 g of the pulverized Mori Cortex Radicis sample was added to 1 L of 100% hexane and extracted three times at room temperature for 24 hours. The extracted sample was filtered with Whatman No. 2 filter paper under reduced pressure, and the filtered extract was concentrated using a vacuum rotary condenser to remove the solvent component, and then a hexane of Mori Cortex Radicis was obtained.

<1-5> Preparation of Hot Water Extract of Mori Cortex Radicis

The root of the dried Mori Cortex Radicis was pulverized with a mixer, and 100 g of the pulverized Mori Cortex Radicis sample was added to 1 L of water and extracted while stirring at 80° C. for 2 hours. The extracted sample was filtered with Whatman No. 2 filter paper under reduced pressure, and the filtered extract was concentrated with a vacuum rotary condenser to remove solvent components, and then a hot water extract of Mori Cortex Radicis was obtained.

<1-6> Preparation of Ultra-High Pressure Extract of Mori Cortex Radicis

The root of the dried Mori Cortex Radicis was pulverized with a mixer, 1 g of the pulverized Mori Cortex Radicis sample and 76 ml of 18% ethanol were placed in a polyethylene pack and sealed, and then extracted using an ultra-high pressure extraction apparatus (Frescal MFP-7000; Mitsubishi Heavy Industries, Tokyo, Japan). Extraction pressure was 320 MPa and extraction time was 5 min. The extracted sample was filtered with Whatman No. 2 filter paper, and the filtered extract was concentrated with a vacuum rotary condenser to remove solvent components to obtain an ultra-high pressure extract of Mori Cortex Radicis.

<1-7> Preparation of Supercritical Fluid Extract of Mori Cortex Radicis

The dried Mori Cortex Radicis was pulverized with a mixer, and 1 g of the pulverized Mori Cortex Radicis sample was filled into a sample cartridge and extracted with a supercritical fluid extraction apparatus (SFX 3560, Isco Inc., Lincoln, Nebr., USA). Supercritical fluid extraction conditions were extraction pressure 40 MPa, extraction temperature 50° C., supercritical carbon dioxide flow rate 60 mL/min, and extraction time 60 min. When the supercritical fluid extraction was completed, the supercritical fluid condition was released by lowering the pressure of the extraction device to obtain a supercritical fluid extract of Mori Cortex Radicis.

<1-8> Preparation of Subcritical Fluid Extract of Mori Cortex Radicis

The dried Mori Cortex Radicis was pulverized with a mixer, and 1 g of the pulverized Mori Cortex Radicis sample was added to 10 mL of distilled water and extracted with a subcritical fluid extractor (DIONEX Accelerated Solvent Extractor 100, DIONEX co., USA). The subcritical fluid extraction condition was extraction pressure 2.5 MPa, the extraction temperature 150° C. and the extraction time 15 minutes. The extracted sample was filtered with Wattman No. 2 filter paper, and the filtered extract was lyophilized at −40° C. to obtain a subcritical fluid extract of Mori Cortex Radicis.

Example 2

Isolation of Morusin and Kuwanon G

<2-1> Isolation of Morusin

The dried Mori Cortex Radicis was pulverized with a mixer, and 100 g of the pulverized Mori Cortex Radicis sample was added to 1 L of 100% ethanol and extracted three times at room temperature for 24 hours. The extracted sample was filtered with Whatman No. 2 filter paper under reduced pressure, and the filtered extract was concentrated using a vacuum rotary condenser to remove the solvent component, and then an ethanol extract of Mori Cortex Radicis was obtained. The ethanol extract was loaded on a column packed with silica gel (silica gel; 70-230 mesh, Merck & Co., Whitehouse Station, N.J., USA), and then collected by using a solvent system mixed with hexane, ethyl acetate and methanol. The collected solution was then divided into eight lower fractions according to the above sorting order. The second fraction was concentrated again with a vacuum rotary evaporator to remove the solvent component. The concentrate was loaded on a column packed with RP-18, and then collected using a solvent system in which water, methanol, and acetonitrile were mixed. And the new collected solution was divided into five lower fractions according to the above sorting order. Morusin, a compound of the following Formula 1, was isolated and purified from fifth fractions:

Formula 1

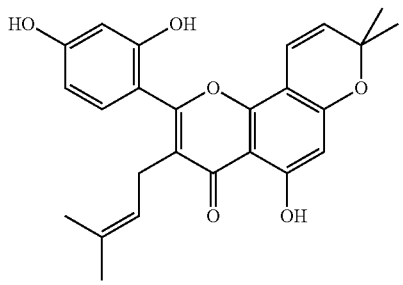

<2-2> Isolation of Kuwanon G

The dried Mori Cortex Radicis was pulverized with a mixer, and 100 g of the pulverized Mori Cortex Radicis sample was added to 1 L of 100% ethanol and extracted three times at room temperature for 24 hours. The extracted sample was filtered with Whatman No. 2 filter paper under reduced pressure, and the filtered extract was concentrated using a vacuum rotary condenser to remove the solvent component, and then an ethanol extract of Mori Cortex Radicis was obtained. The ethanol extract was loaded on a column packed with silica gel (silica gel; 70-230 mesh, Merck & Co., Whitehouse Station, N.J., USA), and then collected by using a solvent system mixed with hexane, ethyl acetate and methanol. And the collected solution was divided into eight lower fractions according to the above sorting order. The sixth fraction was again concentrated on a vacuum rotary evaporator to remove the solvent component. The concentrate was loaded on a column packed with RP-18, and then collected using a solvent system in which water, methanol, and acetonitrile were mixed. The new collected solution was then divided into six lower fractions according to the above sorting order. Kuwanon G, a compounds of Formula 2 were separated and purified in the third fractions:

Formula 2

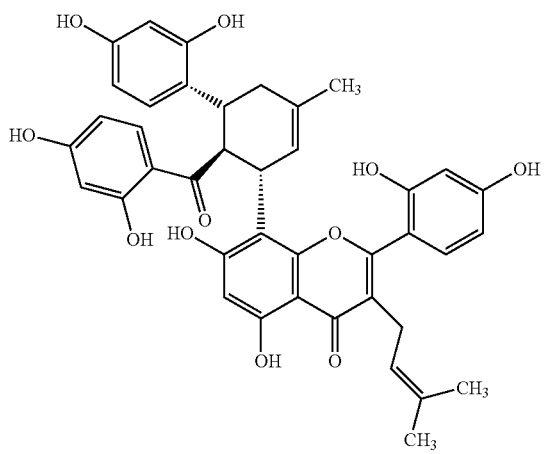

Example 3

Effect of Morusin, Kuwanon G, and Mori Cortex Radicis on Muscle Formation

L6 myoblasts (ATCC, Manassas, Va., USA) were added to a 6-well plate with Dulbecco's modified Eagle's Media (DMEM; Hyclone) containing 10% fetal bovine serum (FBS; Hyclone, Logan, Utah, USA) at a concentration of $2\times10^5$ cells/mL. When the cell density reached about 80 to 85%, the medium in the wells was removed. The ethanol extract of Mori Cortex Radicis (20 μg/mL) prepared in Example 1-2, the hot water extract of Mori Cortex Radicis (20 μg/mL) prepared in Example 1-5, the morusin (5 μM) and the kuwanon G (5 μM) isolated and purified in Example 2 were dissolved in DMEM (Hyclone) containing 2% HS (Hyclone), followed by its treatment to the cells to induce myotube differentiation. Meanwhile, a group treated with 0.01% DMSO instead of the sample was used as a control group. This procedure was carried out for 6 days in two days to differentiate and then dissolved in NP-40 buffer solution (ELPIS-Biotech, Daejeon, Republic of Korea) containing proteinase inhibitor cocktail. The cells dissolved in the buffer solution were transferred to a 1.5-mL tube and centrifuged at 13,000 rpm for 10 minutes to take only a supernatant. The supernatant was quantified using Bradford (Bio-Rad Laboratories Inc., Hercules, Calif., USA). The quantified proteins were boiled for 5 minutes, separated by electrophoresis on 10% SDS-PAGE, and were transferred to the nitrocellulose membrane. A p-mTOR primary antibody (Cellular signaling technology, Beverly, Mass., USA) was diluted with 2.5% bovine serum albumin (BSA) at a ratio of 1:1000 and reacted with proteins transferred to the nitrocellulose membrane for 20 hours at room temperature. The nitrocellulose membrane incubated with the diluted primary antibodies was washed three times for 10 minutes using Tris-buffer Saline Tween 20 (TBST). After washing, the anti-rabbit secondary antibodies (Bethyl Laboratories, Inc., Montgomery, Tex., USA) conjugated with horseradish peroxidase, which recognizes the primary antibody, were diluted to 1:5000 in 2.5% BSA, followed by reaction with the nitrocellulose membrane at room temperature for 2 hours and washing three times for 10 minutes using TBST. Protein bands were developed using ECL western blotting detection reagents (Amersham, Tokyo, Japan), while developed protein bands were identified using G:BOX EF imaging system (Syngene, Cambridge, UK). The results are shown in FIG. 1.

As shown in FIG. 1, it was observed that the expression of p-mTOR in L6 muscle cells was increased by treatment with the ethanol extract and the hot water extract of Mori Cortex Radicis, morusin, and kuwanon G, respectively. This result verifies that the ethanol extract and the hot water extract of Mori Cortex Radicis, morusin, and kuwanon G of the present invention are excellent in increasing muscle synthesis in muscle cells.

Example 4

Effect of Morusin on the Promotion of mRNA Translation in L6 Muscle Cells

The experiment was carried out in the same manner as in Example 3, except that morusin prepared in Example 2-1 was used at a concentration of 0.1 and 1 μM, respectively. Protein bands were identified by treating p-p70S6K and p-4EBP1 primary antibodies (Santa Cruz Biotechnology, Santa Cruz, Calif., USA), which are involved in mRNA translation, instead of p-mTOR primary antibody.

Figure 2:
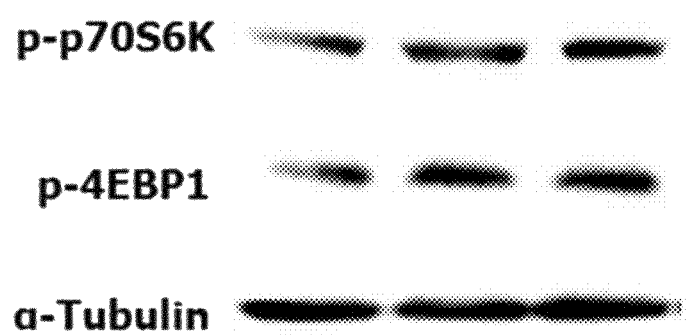
FIG. 2 shows the results of measuring the expression of p-4EBP1 and p-p70S6K proteins after treating with morusin in L6 muscle cells.

As shown in FIG. 2, it was found that the expression of p-p70S6K and p-4EBP1 proteins involved in mRNA translation in L6 muscle cells was increased by treating morusin. This result confirms that morusin according to the present invention promotes the mRNA translation process for muscle synthesis in muscle cells.

Example 5

Effect of Kuwanon G on the Promotion of mRNA Translation in L6 Muscle Cells

Experiments were carried out in the same manner as in Example 3, except that kuwanon G prepared in Example 2-2 was used at a concentration of 1 μM and 5 μM, respectively. The protein band was confirmed by treating p-p70S6K and p-4EBP1 primary antibodies (Santa Cruz Biotechnology), which are involved in the mRNA translation process, instead of the p-mTOR primary antibody.

Figure 3:
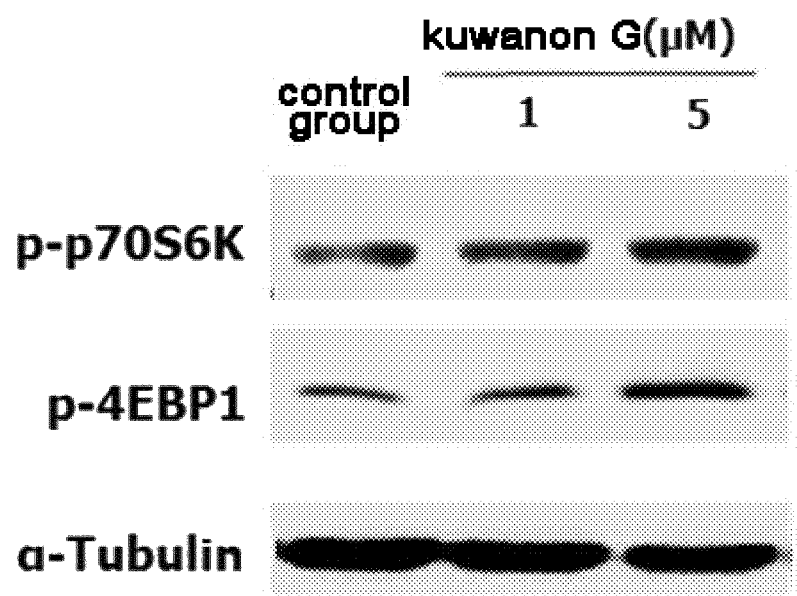
FIG. 3 shows the results of measuring the expression of p-4EBP1 and p-p70S6K proteins after treating with kuwanon G in L6 muscle cells.

As shown in FIG. 3, the expression of p-p70S6K and p-4EBP1 proteins involved in mRNA translation in L6 muscle cells was increased by treating kuwanon G. This result verifies that kuwanon G according to the present invention promotes the mRNA translation process for muscle synthesis in muscle cells.

Example 6

Effect of Extract of Mori Cortex Radicis on the Promotion of mRNA Translation in L6 Muscle Cells The experiment was carried out in the same manner as in Example 3, except that the hexane extract, the ethyl acetate extract, the ethanol extract, and the hot water extract of Mori Cortex Radicis prepared in Examples 1-2 to 1-5 were used at a concentration of 15 μg/mL. The protein band was confirmed by treating p-p70S6K and p-4EBP1 primary antibodies (Santa Cruz Biotechnology), which are involved in the mRNA translation process, instead of the p-mTOR primary antibody.

Figure 4:
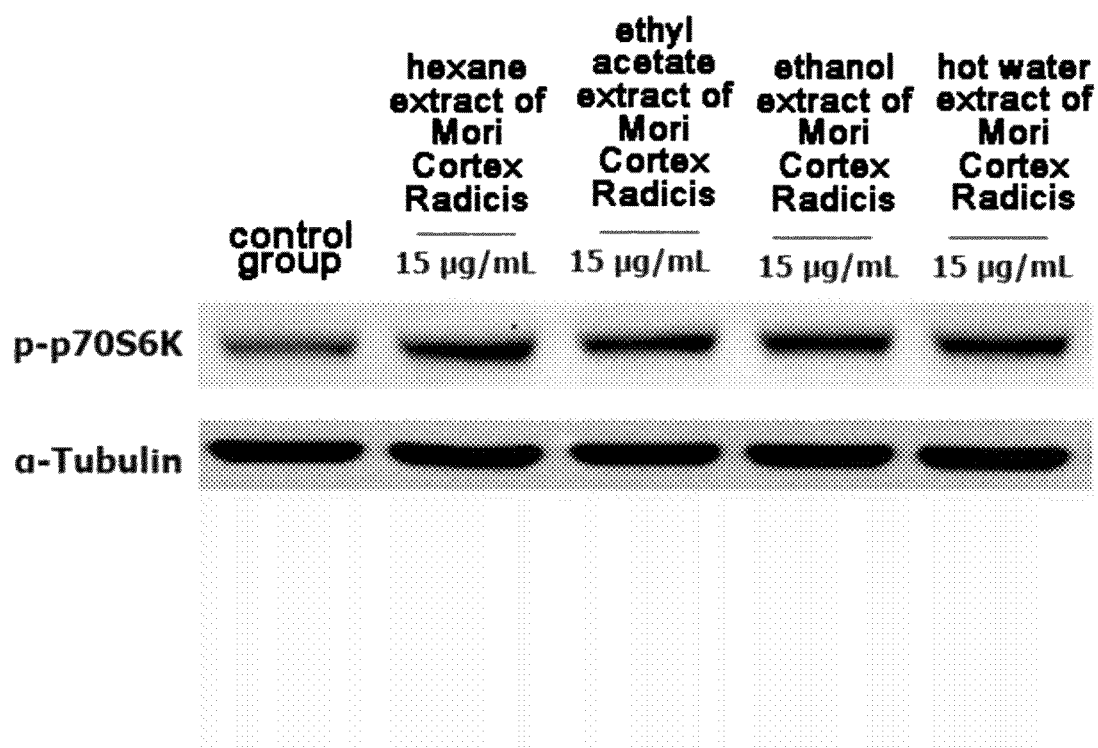
FIG. 4 shows the results of measuring the expression of p-p70S6K protein after treating with the hexane extract, the ethyl acetate extract, the ethanol extract, and the hot water extract of Mori Cortex Radicis in L6 muscle cells.

As shown in FIG. 4, the expression of p-p70S6K protein involved in mRNA translation in the L6 muscle cells was increased by treating the hexane extract, the ethyl acetate extract, the ethanol extract, and the hot water extract of Mori Cortex Radicis, respectively. This result verifies that the hexane extract, the ethyl acetate extract, the ethanol extract, and the hot water extract of Mori Cortex Radicis according to the present invention promote the mRNA translation process for muscle synthesis in muscle cells, respectively.

Example 7

Effect of Morusin on Muscle Differentiation

Muscle cells, L6 myoblasts (ATCC) were added to a 6-well plate at 2×10$^5$ cells/ml together with DMEM (Hyclone) containing 10% FBS (Hyclone). When the cell density reached about 80 to 85%, the medium in the wells was removed. The cells were treated with morusin in Example 2-1 dissolved in DMEM (Hyclone) containing 2% HS (Hyclone) at a concentration of 0.1 and 1 μM, respectively, to induce myotube differentiation. Meanwhile, a group treated with 0.01% DMSO instead of the sample was used as a control group. This procedure was carried out for 6 days in two days to differentiate and total RNA was isolated using TRIzol reagent (Invitrogen. Carlsbad, Calif., USA). The isolated total RNA was quantified using NanoDrop 1000 (Thermo Fisher Scientific Inc., MA, USA). Quantified 16 μL of RNA was synthesized into cDNA using Reverse Transcriptase Premix (ELPIS-Biotech) and PCR machine (Gene Amp PCR System 2700: Applied Biosystems, MA, USA) at 42° C. for 55 minutes and 70° C. for 15 minutes. 4 μL out of 16 μL cDNA was amplified by PCR using the following specific primers (Bioneer, Daejeon, Republic of Korea) and PCR premix (ELPIS-Biotech). PCR was performed by repeating 30 cycles of 95° C. for 30 seconds, 60° C. for 1 minute, and 72° C. for 1 minute.

```
MyoD
Forward primer:
                                         (SEQ ID NO: 1)
5'-TTTCGACTCACCAGACCTGC-3'

Reverse primer:
                                         (SEQ ID NO: 2)
5'-CAGAGCCTGCAGACCTTCAA-3'

Myogenin
Forward primer:
                                         (SEQ ID NO: 3)
5'-TTTCGCACCTGATGGACCTG-3'

Reverse primer:
                                         (SEQ ID NO: 4)
5'-CTTTCTTGAGCCTGCGCTTC-3'

β-Actin:
Forward primer:
                                         (SEQ ID NO: 5)
5'-AGCCATGTACGTAGCCATCC-3'

Reverse primer:
                                         (SEQ ID NO: 6)
5'-CTCTCAGCTGTGGTGCTGAA-3'
```

PCR-amplified cDNA was separated by electrophoresis on 1.5% agarose gel and cDNA band was identified using G:BOX EF imaging system (Syngene). The results are shown in FIG. 5.

Figure 5:
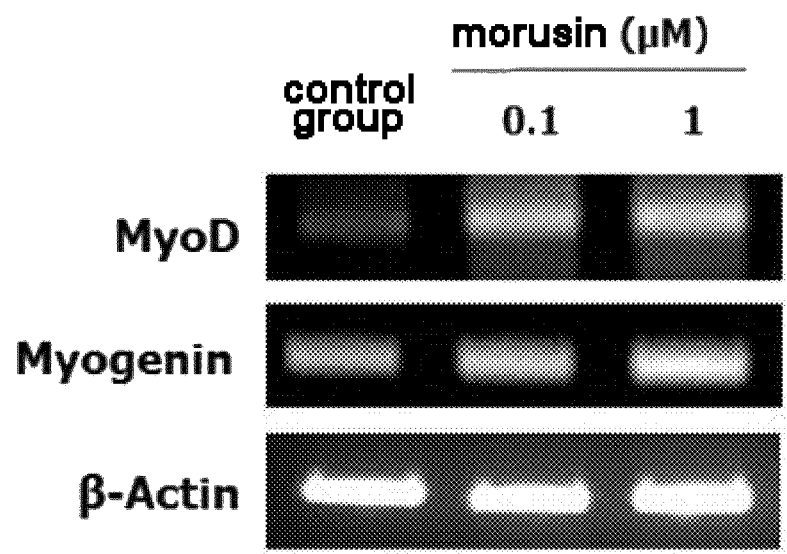
FIG. 5 shows the results of measuring the mRNA expression of MyoD and myogenin after treating with morusin in L6 muscle cells.

As shown in FIG. 5, it was observed that the expression of MyoD and myogenin mRNA was increased in L6 muscle cells by treating morusin. This result verifies that morusin according to the present invention is excellent in promoting muscle differentiation in muscle cells.

Example 8

Effect of Kuwanon G on Muscle Differentiation

L6 myoblast (ATCC) were cultured in the same manner as in Example 7. The cells were treated with kuwanon G, which was isolated and purified in Example 2-2 and was dissolved in DMEM (Hyclone) containing 2% HS (Hyclone), at a concentration of 1 μM and 5 μM, respectively, to induce myotube differentiation. Meanwhile, a group treated with 0.01% DMSO instead of the sample was used as a control group. RT-PCR was performed in the same manner as in Example 7, after proceeding this procedure for 6 days in 2 days to differentiate.

Figure 6:
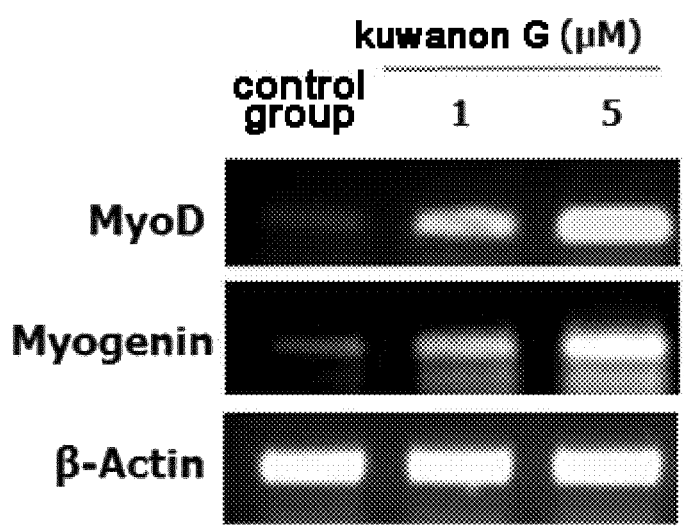
FIG. 6 shows the results of measuring the mRNA expression of MyoD and myogenin after treating with kuwanon G in L6 muscle cells.

As shown in FIG. 6, it was observed that the expression of MyoD and myogenin mRNA was increased in L6 muscle cells by treating kuwanon G. This result verifies that kuwanon G according to the present invention is excellent in promoting muscle differentiation in muscle cells.

Example 9

Effect of Extract of Mori Cortex Radicis on Muscle Differentiation

L6 myoblast (ATCC) was cultured in the same manner as in Example 7. The cells were treated with the hexane extract, the ethyl acetate extract, the ethanol extract, and the hot water extract of Mori Cortex Radicis, which were prepared in Example 1-2 to 1-5 and were dissolved in DMEM (Hyclone) containing 2% HS (Hyclone), at a concentration of 15 μg/mL, respectively, to induce myotube differentiation. Meanwhile, a group treated with 0.01% DMSO instead of the sample was used as a control group. RT-PCR was performed in the same manner as in Example 7, after proceeding this procedure for 6 days in 2 days to differentiate.

Figure 7:
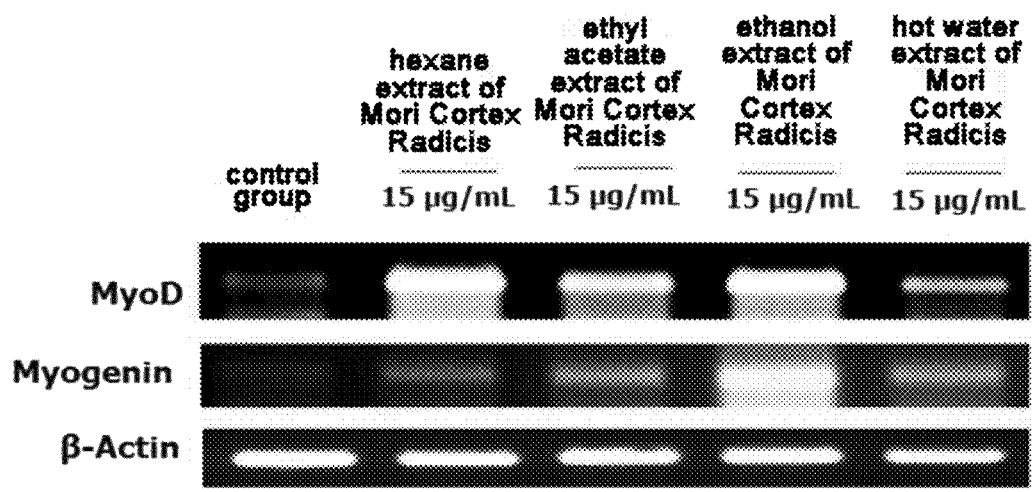
FIG. 7 shows the results of measuring the mRNA expression of MyoD and myogenin by treating with the hexane extract, the ethyl acetate extract, the ethanol extract, and the hot water extract of Mori Cortex Radicis in L6 muscle cells.

As shown in FIG. 7, it was observed that the expression of MyoD and myogenin mRNA was increased in L6 muscle cells by treating the hexane extract, the ethyl acetate extract, the ethanol extract, and the hot water extract of Mori Cortex Radicis, respectively. This result verifies that the extract of Mori Cortex Radicis according to the present invention is excellent in promoting muscle differentiation in muscle cells.

Example 10

Effect of Morusin on the Inhibition of Muscle Protein Degradation

L6 myoblast (ATCC) was added to a 6-well plate at $2 \times 10^5$ cells/ml together with DMEM (Hyclone) containing 10% FBS (Hyclone). When the cell density reached about 80% to 85%, the medium in the wells was removed and myotube differentiation was induced by treating the cells with DMEM (Hyclone) containing 2% HS (Hyclone). The medium was replaced with fresh medium every two days and the differentiation was carried out for a total of 6 days. After differentiation, 0.1 μM and 1 μM of morusin prepared in Example 2-1 were respectively dissolved in DMEM (Hyclone) containing 50 ng/mL tumor necrosis factor alph (TNF-α; PeproTech, Rocky Hills, N.J., USA), followed by their treatment on the cells. After 6 hours, total RNA was isolated using TRIzol reagent (Invitrogen). The isolated total RNA was quantified using NanoDrop 1000 (Thermo Fisher Scientific Inc.). The quantified 16 μL of RNA was synthesized into cDNA using Reverse Transcriptase Premix (ELPIS-Biotech) and PCR machine (Gene Amp PCR System 2700: Applied Biosystems) at 42° C. for 55 minutes and at 70° C. for 15 minutes. The PCR was performed by repeating 30 cycles at 95° C. for 30 seconds, at 60° C. for 1 minute and at 72° C. for 1 minute with 4 μl of 16 μl cDNA, the following specific primers (Bioneer), and PCR premix (ELPIS-Biotech):

```
Atrogin-1
Forward primer:
                                        (SEQ ID NO: 7)
5'-CCCTGAGTGGCATCGCCCAA-3'

Reverse primer:
                                        (SEQ ID NO: 8)
5'-AGGTCCCGCCCATCGCTCA-3'

MuRF-1
Forward primer:
                                        (SEQ ID NO: 9)
5'-GAAATGCTATGCAGAACCTG-3'

Reverse primer:
                                        (SEQ ID NO: 10)
5'-ATTCCTGCTTGTAGATGTCG-3'

β-Actin:
Forward primer:
                                        (SEQ ID NO: 11)
5'-AGCCATGTACGTAGCCATCC-3'

Reverse primer:
                                        (SEQ ID NO: 12)
5'-CTCTCAGCTGTGGTGCTGAA-3'
```

PCR-amplified cDNA were separated by electrophoresis on 1.5% agarose gel, and cDNA band was identified using G:BOX EF imaging system (Syngene). The results are shown in FIG. 8.

Figure 8:
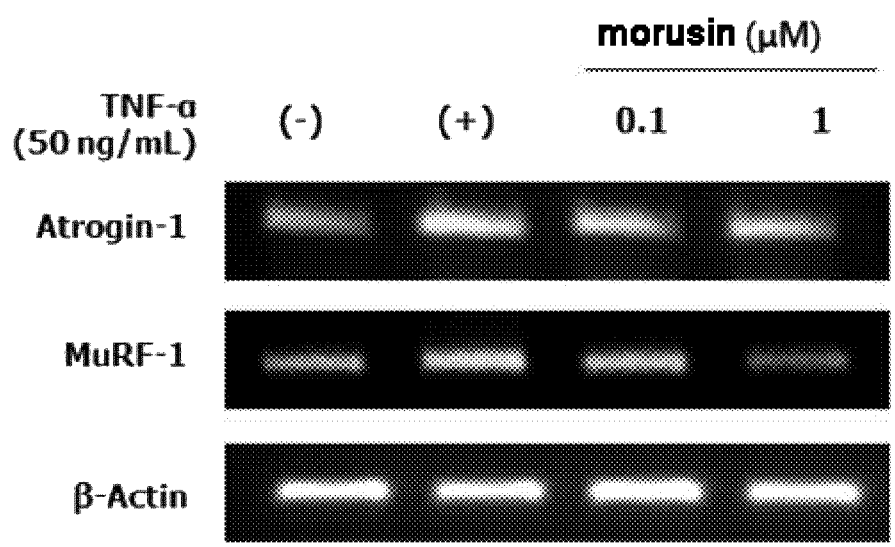
FIG. 8 shows the results of measuring the mRNA expression of atrogin-1 and MuRF-1 by treating with morusin in L6 muscle cells.

As shown in FIG. 8, it was found that mRNA expression of atrogin-1 and MuRF-1 in L6 muscle cells was decreased by treating morusin. This result verifies that morusin according to the present invention is excellent in inhibiting the degradation of muscle proteins in muscle cells.

Example 11

Effect of Kuwanon G on the Inhibition of Muscle Protein Degradation

In the same manner as in Example 10, L6 myoblast (ATCC) were treated with DMEM (Hyclone) containing 2% HS (Hyclone) to induce microtube differentiation, followed by dissolving Kuwanon G, which was isolated and purified in Example 2-2, in DMEM (Hyclone) containing 50 ng/mL TNF-α (PeproTech). Then, RT-PCR was performed in the same manner as in Example 10.

Figure 9:
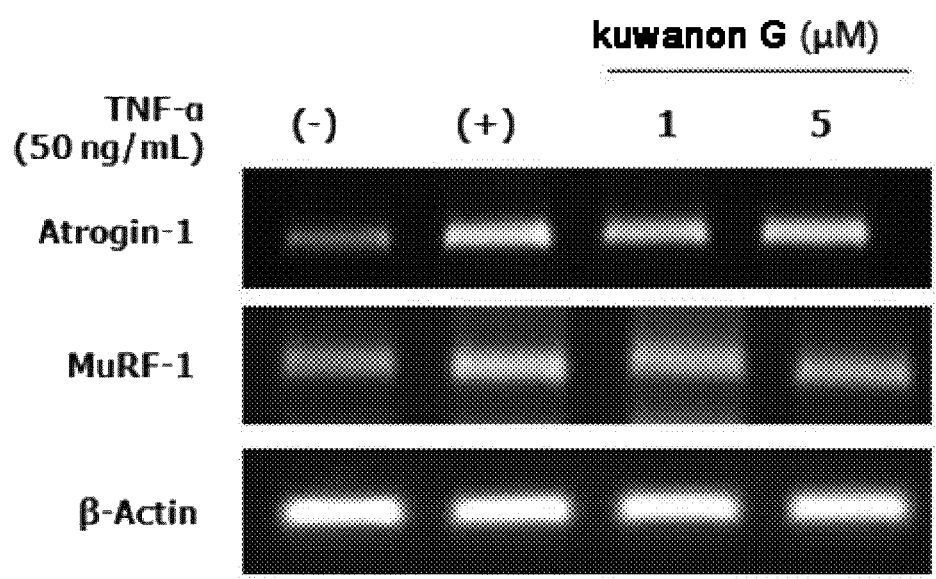
FIG. 9 shows the results of measuring the mRNA expression of atrogin-1 and MuRF-1 by treating with kuwanon G in L6 muscle cells.

As shown in FIG. 9, it was found that mRNA expression of atrogin-1 and MuRF-1 in L6 muscle cells was decreased by treating kuwanon G. This result verifies that kuwanon G according to the present invention is excellent in inhibiting the degradation of muscle proteins in muscle cells.

Example 12

Effect of Extract of Mori Cortex Radicis on the Inhibition of Muscle Protein Degradation The muscle cells cultured in the same manner as in Example 10 were treated with DMEM (Hyclone) containing 2% HS (Hyclone) to induce myotube differentiation. The hexane extract, the ethyl acetate extract, the ethanol extract, and the hot water extract of Mori Cortex Radicis prepared in Examples 1-2 to 1-5 was dissolved in the DMEM (Hyclone) containing 50 ng/mL TNF-α (PeproTech) at a concentration of 10 μg/mL, respectively, and then RT-PCR was performed in the same manner as in Example 10.

Figure 10:
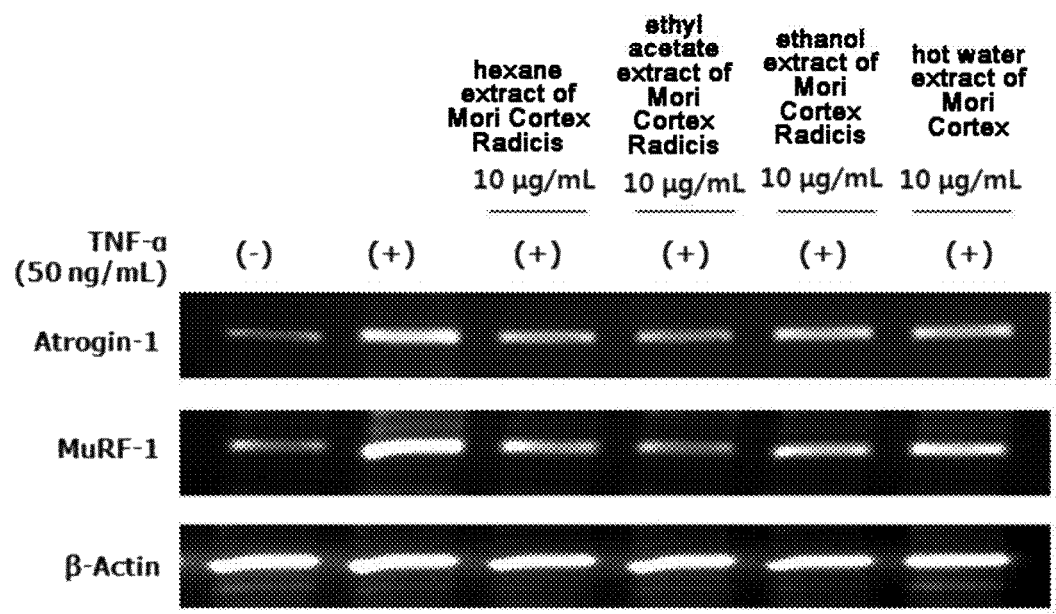
FIG. 10 shows the results of measuring the mRNA expression of atrogin-1 and MuRF-1 by treating with the hexane extract, the ethyl acetate extract, the ethanol extract, and the hot water extract of Mori Cortex Radicis in L6 muscle cells.

As shown in FIG. 10, it was found that mRNA expression of atrogin-1 and MuRF-1 in L6 muscle cells was decreased by treating the hexane extract, the ethyl acetate extract, the ethanol extract, and the hot water extract of Mori Cortex Radicis, respectively. This result verifies that the extract of Mori Cortex Radicis according to the present invention is excellent in inhibiting the degradation of muscle proteins in muscle cells.

Example 13

Effect of High Pressure Extracts of Mori Cortex Radicis on Muscle Formation

The muscle cells were treated with the ultra-high pressure extract of Mori Cortex Radicis prepared in Example 1-6, the supercritical fluid extract of Mori Cortex Radicis prepared in Example 1-7, and the subcritical fluid extract of Mori Cortex Radicis prepared in Example 1-8, respectively, at a concentration of 20 ppm, in the same manner as in Example 3. The p-mTOR protein band was developed using ECL Western Blotting Detection Reagents (Amersham, Tokyo, Japan) and a density of the developed protein band was measured using G:BOX EF imaging system (Syngene, Cambridge, UK). The relative density of the protein bands of the experimental group treated with the sample was expressed as a percentage (%), while the density of the control protein band was designated as 100%.

The results are shown in Table 1 below.

TABLE 1

Effect of high pressure extracts of Mori Cortex Radicis on the increase of the expression level of p-mTOR protein

| Experimental group | Relative density (%) |
|---|---|
| Control group | 100 |
| Example 1-6 | 142 |
| Example 1-7 | 131 |
| Example 1-8 | 136 |

As shown in Table 1, it was confirmed that the ultra-high pressure extract, the supercritical fluid extract, and the subcritical fluid extract of Mori Cortex Radicis increase the protein expression of the major gene p-mTOR which is involved in the improvement of muscular function.

Example 14

Evaluation on the Effect of Increasing Muscle Mass in Animal Models

Five-week-old Wistar rats were adapted for 1 week and 100 ng/g of TNF-α was supplied for 2 weeks to induce muscular atrophy. Then, groups were randomly assigned on the basis of body weight and divided into five groups of 8 rats per each group. 500 mg/kg body weight of the ethanol extract of Mori Cortex Radicis prepared in Example 1-2, 500 mg/kg body weight of the hot-water extract of Mori Cortex Radicis prepared in Example 1-5, 300 mg/kg body weight of the morusin prepared in Example 2-1, and 300 mg/kg body weight of the kuwanon G prepared in Example 2-2 were suspended in 0.25% carboxymethylcellulose, respectively, followed by their administration on experimental groups once a day for 8 weeks at regular time. A control group was administered with TNF-α suspended in the same amount of 0.25% carboxymethyl cellulose ingested by the experimental groups.

After 8 weeks of administration, the muscles under the right calf were excised and weighed with microbalance (Mettler PE 160, USA). As a result, as shown in Table 2, the weight of muscle was significantly ($p<0.01$) increased by 20.78%, 17.35%, 23.97%, and 22.60% in the groups administered with the ethanol extract and the hot-water extract of Mori Cortex Radicis, morusin, and kuwanon G, respectively. These results confirm that the extracts of Mori Cortex Radicis, and morusin & kuwanon G isolated from Mori Cortex Radicis according to the present invention are effective for increasing muscle mass.

TABLE 2

Weight of calf muscle per treated material

| Experimental groups | Average calf muscle weight (mg) |
|---|---|
| Control group | 438 ± 20.8 |
| Ethanol extract of Mori Cortex Radicis | 529 ± 30.5 |
| Hot water extract of Mori Cortex Radicis | 514 ± 19.5 |
| Morusin | 543 ± 32.9 |
| Kuwanon G | 537 ± 15.2 |

Hereinafter, there are disclosed preparation examples for preparing a pharmaceutical composition, a food composition, or a cosmetic composition, the compositions comprising, as an active ingredient, morusin, kuwanon G, or the extract of Mori Cortex Radicis of Examples 1 & 2. However, these preparation examples are not intended to limit the present invention by any means, but merely to be illustrative. The pharmaceutical, food or cosmetic compositions of Preparation Examples 1 to 3, each of which comprises morusin, kuwanon G, or the extract of Mori Cortex Radicis and is excellent in preventing or treating muscle diseases or improving muscular function, were prepared according to the conventional methods using the following components and composition ratios.

<Preparation Example 1> Medicine

<1-1> Powder 50 mg of morusin, kuwanon G, or the extract of Mori Cortex Radicis of Examples 1 and 2, and 2 g of crystalline cellulose were mixed thoroughly and then, filled and sealed in a sealed package to obtain a powder preparation.

<1-2> Tablets 50 mg of morusin, kuwanon G, or the extract of Mori Cortex Radicis of Examples 1 and 2, 400 mg of crystalline cellulose, and 5 mg of magnesium stearate were mixed thoroughly and then formulated according to conventional methods to obtain a tablet preparation.

<1-3> Capsules 30 mg of morusin, kuwanon G. or the extract of Mori Cortex Radicis of Examples 1 and 2, 100 mg of whey protein, 400 mg of crystalline cellulose, and 6 mg of magnesium stearate were mixed thoroughly and then filled in a gelatin capsule according to conventional methods to obtain a capsule preparation.

<1-4> Injection

According to the conventional injection preparation method, the active ingredient was dissolved in distilled water for injection and the pH was adjusted to about 7.5. Subsequently, 100 mg of morusin or kuwanon G of Example 2, distilled water for injection, and pH adjusting agent were mixed. The mixture was filled in a 2 mL ampule and sterilized to prepare an injection.

<Preparation Example 2> Food

<2-1> Preparation of Health Food 1000 mg of morusin, kuwanon G, or the extract of Mori Cortex Radicis of Examples 1 and 2, 70 μg of vitamin A acetate, 1.0 mg of vitamin E, 0.13 mg of vitamin B1, 0.15 mg of vitamin B2, 0.5 mg of vitamin B6, 0.2 μg of vitamin B12, 10 mg of vitamin C, 10 μg of biotin, 1.7 mg of Nicotinic amide, 50 μg of folic acid, 0.5 mg of calcium pantothenate, 1.75 mg of ferrous sulfate, 0.82 mg of zinc oxide, 25.3 mg of magnesium carbonate, 15 mg of potassium monophosphate, 55 mg of dibasic calcium phosphate, 90 mg of potassium citrate, 100 mg of calcium carbonate, and 24.8 mg of magnesium chloride may be mixed to prepare a health food. The composition ratio may be arbitrarily changed. According to general health food manufacturing methods, after mixing the above components, granules are prepared for use in the manufacture of a health food composition according to a conventional method.

<2-2> Preparation of Health Drinks

According to general health drink manufacturing methods, 1000 mg of morusin, kuwanon G, or the extract of Mori Cortex Radicis of Examples 1and 2, 1000 mg of citric acid, 100 g of oligosaccharide, 2 g of plum concentrate and 1 g of taurine, and purified water were mixed to make 900 ml in total. After stirring for 1 hour at 85° C., the resulting solution is was filtered and placed in a sterilized 2 L container, sealed, sterilized and refrigerated for use in the manufacture of a health beverage composition.

<2-3> Chewing Gum 20 wt % of gum base, 76.9 wt % of sugar, 1 wt % of flavor, 2 wt % of water and 0.1 wt % of morusin, kuwanon G, or the extract of Mori Cortex Radicis of Examples 1 and 2 were mixed to be prepared into a chewing gum according to well-known methods.

<2-4> Candy 60 wt % of sugar, 39.8 wt % of starch syrup, 0.1 wt % of flavor and 0.1 wt % of morusin, kuwanon G, or the extract of Mori Cortex Radicis of Examples 1 and 2 were mixed to be prepared into candy according to well-known methods.

<2-5> Biscuit 25.59 wt % of first grade soft flour, 22.22 wt % of first grade plain flour, 4.80 wt % of refined sugar, 0.73 wt % of salt, 0.78 wt % of glucose, 11.78 wt % of palm shortening, 1.54 wt % of ammonium, 0.17 wt % of sodium bicarbonate, 0.16 wt % of sodium sulfite, 1.45 wt % rice powder, 0.0001 wt % of vitamin B, 0.04 wt % of milk flavor, 20.6998 wt % of water, 1.16 wt % of whole milk powder, 0.29 wt % of alternative milk powder, 0.03 wt % of calcium phosphate 1, 0.29 wt % of sulfuric salt, 7.27 wt % of spray milk, and 1 wt % of morusin, kuwanon G, or the extract of Mori Cortex Radicis of Examples 1 and 2 were mixed to be prepared into biscuit according to well-known methods.

<Preparation Example 3> Cosmetics

<3-1> Nourishing Lotion (Milk Lotion)

According to conventional methods, nourishing lotion was prepared with morusin, kuwanon G, or the extract of Mori Cortex Radicis of Examples 1 and 2 and the following components at a ratio as shown in Table 3 below.

TABLE 3

| Composition ingredients | Preparation Example 3-1 (wt %) |
|---|---|
| Morusin, kuwanon G, or the extract of Mori Cortex Radicis | 2.0 |
| Squalane | 5.0 |
| Wax | 4.0 |
| Polysorbate 60 | 1.5 |
| Sorbitan sesquioleate | 1.5 |
| Liquid paraffin | 0.5 |
| Caprylic/capric triglyceride | 5.0 |
| Glycerin | 3.0 |
| Butylene glycol | 3.0 |
| Propylene glycol | 3.0 |
| Carboxyvinyl polymer | 0.1 |
| Triethanolamine | 0.2 |
| Preservatives, coloring agent, fragrance | q.s. |
| Purified water | To 100 |

<3-2> Softening Lotion (Skin Lotion)

According to conventional methods, skin lotion was prepared with morusin, kuwanon G, or the extract of Mori Cortex Radicis of Examples 1 and 2 and the following components at a ratio as shown in Table 4 below.

TABLE 4

| Composition ingredients | Preparation Example 3-2 (wt %) |
|---|---|
| Morusin, kuwanon G, or The extract of Mori Cortex Radicis | 2.0 |
| Glycerin | 3.0 |

TABLE 4-continued

| Composition ingredients | Preparation Example 3-2 (wt %) |
|---|---|
| Butylene glycol | 2.0 |
| Propylene glycol | 2.0 |
| Carboxyvinyl polymer | 0.1 |
| PEG 12 Nonyl phenyl ether | 0.2 |
| Polysorbate 80 | 0.4 |
| Ethanol | 10.0 |
| Triethanolamine | 0.1 |
| Preservatives, coloring agent, fragrance | q.s. |
| Purified water | To 100 |

<3-3> Nourishing Cream

According to conventional methods, nutritional cream was prepared with morusin, kuwanon G, or the extract of Mori Cortex Radicis of Example 1 and 2 and the following components at a ratio as shown in Table 5 below.

TABLE 5

| Compounding ingredient | Preparation Example 3-3 (wt %) |
|---|---|
| Morusin, kuwanon G, or the extract of Mori Cortex Radicis | 2.0 |
| Polysorbate 60 | 1.5 |
| Sorbitan sesquioleate | 0.5 |
| PEG60 Hardened castor oil | 2.0 |
| Liquid paraffin | 10 |
| Squalane | 5.0 |
| Caprylic/capric triglyceride | 5.0 |
| Glycerin | 5.0 |
| Butylene glycol | 3.0 |
| Propylene glycol | 3.0 |
| Triethanolamine | 0.2 |
| Preservatives | q.s. |
| Coloring agent | q.s. |
| Fragrance | q.s. |
| Purified water | To 100 |

<3-4> Massage Cream

According to conventional methods, massage cream was prepared with morusin, kuwanon G, or the extract of Mori Cortex Radicis of Examples 1 and 2 and the following components at a ratio as shown in Table 6 below.

TABLE 6

| Composition ingredients | Preparation Example 3-4 (wt %) |
|---|---|
| Morusin, kuwanon G, or the extract of Mori Cortex Radicis | 1.0 |
| Wax | 10.0 |
| Polysorbate 60 | 1.5 |
| PEG60 Hardened castor oil | 2.0 |
| Sorbitan sesquioleate | 0.8 |
| Liquid paraffin | 40.0 |
| Squalane | 5.0 |
| Caprylic/capric triglyceride | 4.0 |
| Glycerin | 5.0 |
| Butylene glycol | 3.0 |
| Propylene glycol | 3.0 |
| Triethanolamine | 0.2 |
| Preservatives, coloring agent, fragrance | q.s. |
| Purified water | To 100 |

<3-5> Pack

According to conventional methods, a pack was prepared with morusin, kuwanon G, or the extract of Mori Cortex Radicis of Examples 1 and 2 and the following components at a ratio as shown in Table 7 below.

TABLE 7

| Composition ingredients | Preparation Example 3-5 (wt %) |
| --- | --- |
| Morusin, kuwanon G, or the extract of Mori Cortex Radicis | 1.0 |
| Polyvinyl alcohol | 13.0 |
| Sodium carboxymethylcellulose | 0.2 |
| Glycerin | 5.0 |
| Allantoin | 0.1 |
| Ethanol | 6.0 |
| PEG12 nonyl phenyl ether | 0.3 |
| Polysorbate 60 | 0.3 |
| Preservatives, coloring agent, fragrance | q.s. |
| Purified water | To 100 |

<3-6> Gel

According to conventional methods, a gel was prepared with morusin, kuwanon G, or the extract of Mori Cortex Radicis of Examples 1 and 2 and the following components at a ratio as shown in Table 8 below.

TABLE 8

| Composition ingredients | Preparation Example 3-6 (wt %) |
| --- | --- |
| Morusin, kuwanon G, or the extract of Mori Cortex Radicis | 0.5 |
| Ethylenediamine sodium acetate | 0.05 |
| Glycerin | 5.0 |
| Carboxyvinyl polymer | 0.3 |
| Ethanol | 5.0 |
| PEG60 Hardened castor oil | 0.5 |
| Triethanolamine | 0.3 |
| Preservatives, coloring agent, fragrance | q.s. |
| Purified water | To 100 |

What is claimed is:

1. A method for treating a muscle disease induced by muscle wasting or degeneration in a subject, the method comprising administering to the subject a composition consisting essentially of at least one compound selected from the group consisting of:

(1) a compound of Formula 1:

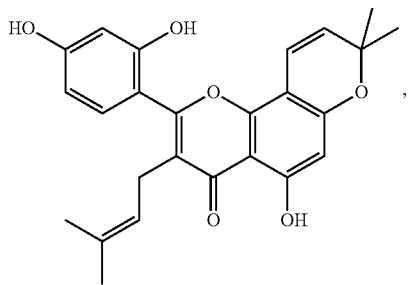 [SMILES: CC(C)=CCc1c(-c2ccc(O)cc2O)oc2c3c(cc(O)c2c1=O)OC(C)(C)C=C3]

(2) a compound of Formula 2

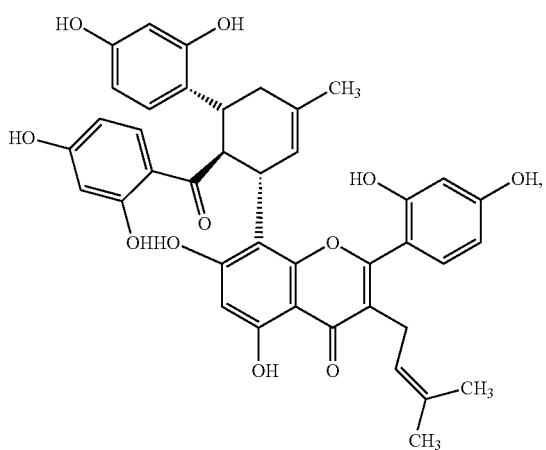

and (3) an extract of Mori Cortex Radicis, wherein the compound is an active ingredient administered in an amount effective for enhancing muscle mass growth to treat the muscle disease induced by muscle wasting or degeneration, and wherein the muscle disease induced by muscle wasting or degeneration is selected from the group consisting of atony, muscular atrophy, muscular dystrophy, muscular degeneration, muscular spasticity, amyotrophic lateral sclerosis, myasthenia gravis, cachexia and sarcopenia.

2. The method of claim 1, wherein the composition is a pharmaceutical composition.

3. The method of claim 1, wherein the composition is a food composition or a cosmetic composition.

4. The method of claim 1, wherein the compound defined by Formula 1 or 2 is isolated from the extract of Mori Cortex Radicis.

5. The method of claim 1, wherein the Mori Cortex Radicis is a dried root bark of a plant belonging to a plant of family Moraceae and genus *Morus* spp.

6. The method of claim 1, wherein the extract of Mori Cortex Radicis is an extract obtained using at least one solvent selected from the group consisting of water, an organic solvent having 1 to 6 carbon atoms, a subcritical fluid, a supercritical fluid, and a mixture thereof.

7. The method of claim 6, wherein the organic solvent having 1 to 6 carbon atoms is selected from the group consisting of alcohol having 1 to 6 carbon atoms, acetone, ether, benzene, chloroform, ethyl acetate, methylene chloride, hexane, cyclohexane, and petroleum ether.

8. The method of claim 1, wherein the extract of Mori Cortex Radicis is obtained by extracting Mori Cortex Radicis under an ultra-high pressure of 100 MPa to 1000 Mpa.

* * * * *

```
                        SEQUENCE LISTING

<160> NUMBER OF SEQ ID NOS: 10

<210> SEQ ID NO 1
<211> LENGTH: 20
<212> TYPE: DNA
<213> ORGANISM: Artificial Sequence
<220> FEATURE:
<223> OTHER INFORMATION: MyoD primer forward

<400> SEQUENCE: 1
tttcgactca ccagacctgc                                              20

<210> SEQ ID NO 2
<211> LENGTH: 20
<212> TYPE: DNA
<213> ORGANISM: Artificial Sequence
<220> FEATURE:
<223> OTHER INFORMATION: MyoD primer reverse

<400> SEQUENCE: 2
cagagcctgc agaccttcaa                                              20

<210> SEQ ID NO 3
<211> LENGTH: 20
<212> TYPE: DNA
<213> ORGANISM: Artificial Sequence
<220> FEATURE:
<223> OTHER INFORMATION: Myogenin primer forward

<400> SEQUENCE: 3
tttcgcacct gatggacctg                                              20

<210> SEQ ID NO 4
<211> LENGTH: 20
<212> TYPE: DNA
<213> ORGANISM: Artificial Sequence
<220> FEATURE:
<223> OTHER INFORMATION: Myogenin primer reverse

<400> SEQUENCE: 4
ctttcttgag cctgcgcttc                                              20

<210> SEQ ID NO 5
<211> LENGTH: 20
<212> TYPE: DNA
<213> ORGANISM: Artificial Sequence
<220> FEATURE:
```

```
<223> OTHER INFORMATION: beta-actin primer forward

<400> SEQUENCE: 5
agccatgtac gtagccatcc                                                   20

<210> SEQ ID NO 6
<211> LENGTH: 20
<212> TYPE: DNA
<213> ORGANISM: Artificial Sequence
<220> FEATURE:
<223> OTHER INFORMATION: beta-actin primer reverse

<400> SEQUENCE: 6
ctctcagctg tggtgctgaa                                                   20

<210> SEQ ID NO 7
<211> LENGTH: 20
<212> TYPE: DNA
<213> ORGANISM: Artificial Sequence
<220> FEATURE:
<223> OTHER INFORMATION: Atrogin-1 primer forward

<400> SEQUENCE: 7
ccctgagtgg catcgcccaa                                                   20

<210> SEQ ID NO 8
<211> LENGTH: 19
<212> TYPE: DNA
<213> ORGANISM: Artificial Sequence
<220> FEATURE:
<223> OTHER INFORMATION: Atrogin-1 primer reverse

<400> SEQUENCE: 8
aggtcccgcc catcgctca                                                    19

<210> SEQ ID NO 9
<211> LENGTH: 20
<212> TYPE: DNA
<213> ORGANISM: Artificial Sequence
<220> FEATURE:
<223> OTHER INFORMATION: MuRF-1 primer forward

<400> SEQUENCE: 9
gaaatgctat gcagaacctg                                                   20

<210> SEQ ID NO 10
<211> LENGTH: 20
<212> TYPE: DNA
<213> ORGANISM: Artificial Sequence
<220> FEATURE:
<223> OTHER INFORMATION: MuRF-1 primer reverse

<400> SEQUENCE: 10
attcctgctt gtagatgtcg                                                   20
```